United States Patent
Van Der Graaf et al.

(10) Patent No.: US 10,676,452 B2
(45) Date of Patent: Jun. 9, 2020

(54) COMPOUND FOR THE PROPHYLAXIS OR TREATMENT OF ORGAN DAMAGE

(71) Applicant: Sulfateq B.V., Groningen (NL)

(72) Inventors: Adrianus Cornelis Van Der Graaf, Groningen (NL); Robert Henk Henning, Groningen (NL); Leo Edwin Deelman, Peize (NL); Gerrit Jan Willem Euverink, Haren (NL)

(73) Assignee: Sulfateq B.V., Groningen (NL)

( * ) Notice: Subject to any disclaimer, the term of this patent is extended or adjusted under 35 U.S.C. 154(b) by 0 days.

(21) Appl. No.: 15/576,290

(22) PCT Filed: May 12, 2016

(86) PCT No.: PCT/EP2016/060731
§ 371 (c)(1),
(2) Date: Nov. 22, 2017

(87) PCT Pub. No.: WO2016/188766
PCT Pub. Date: Dec. 1, 2016

(65) Prior Publication Data
US 2018/0170892 A1 Jun. 21, 2018

(30) Foreign Application Priority Data

May 22, 2015 (NL) ..................................... 2014843

(51) Int. Cl.
| | |
|---|---|
| C07D 311/72 | (2006.01) |
| A61K 31/353 | (2006.01) |
| A61P 13/12 | (2006.01) |
| C07D 405/06 | (2006.01) |

(52) U.S. Cl.
CPC .......... *C07D 311/72* (2013.01); *A61K 31/353* (2013.01); *A61P 13/12* (2018.01); *C07D 405/06* (2013.01)

(58) Field of Classification Search
None
See application file for complete search history.

(56) References Cited

U.S. PATENT DOCUMENTS

| | | |
|---|---|---|
| 4,681,890 A | 7/1987 | Kanehira et al. |
| 5,508,450 A | 4/1996 | Ohuchida et al. |
| 5,602,133 A | 2/1997 | Antonucci et al. |
| 5,889,045 A | 3/1999 | Muller et al. |
| 6,335,445 B1 | 1/2002 | Chabrier De Lassauniere et al. |
| 6,727,239 B1 | 4/2004 | Chabrier De Lassauniere et al. |
| 7,456,205 B2 | 11/2008 | Yang et al. |

FOREIGN PATENT DOCUMENTS

| | | |
|---|---|---|
| EP | 0202580 A2 | 11/1986 |
| EP | 1650206 A1 | 4/2006 |
| WO | 88/08424 A1 | 11/1988 |
| WO | 97/41121 A1 | 11/1997 |
| WO | 03/024943 A2 | 3/2003 |
| WO | 2014/011047 A1 | 1/2014 |
| WO | 2014/098586 A1 | 6/2014 |
| WO | WO-2014098586 A1 * | 6/2014 ........... C07D 311/74 |

OTHER PUBLICATIONS

Kashihara, N. Curr Med. Chem. (2010); 17(34):4256-4269.*
International Search Report for PCT/EP2016/060731 dated Sep. 26, 2016.
International Preliminary Report on Patentability for PCT/EP2016/060731 dated Nov. 28, 2017.
Berge et al, "Pharmaceutical Salts", Journal of Pharmaceutical Science 1977;66, pp. 1-19.
Jacobsen et al, "2-(Aminomethyl)chromans that inhibit iron-dependent lipid peroxidation and protect against central nervous system trauma and ischemia", Journal of Medicinal Chemistry, American Chemical Society, US, vol. 35, No. 23, Jan. 1, 1992, pp. 4464-4472.
Koufaki et al, "Synthesis of a second generation chroman/catechol hybrids and evaluation of their activity in protecting neuronal cells from oxidative stress-induced cell death", Bioorganic & Medicinal Chemistry, Pergamon, GB, vol. 18, No. 11, pp. 3898-3909, (2010).
Koufaki et al, "Chroman/Catechol Hybrids: Synthesis and Evaluation of Their Activity against Oxidative Stress Induced Cellular Damage", Journal of Medicinal Chemistry, Jan. 1, 2006, vol. 49, No. 1, pp. 300-306.
Ogura et al, "Oxidative Stress and Organ Damages", Current Hypertension Reports, GB, Aug. 1, 2014, vol. 16, No. 8, 452, pp. 1-5.
Wardle, "Cellular oxidative processes in relation to renal disease.", American Journal of Nephrology, Jan. 2005, vol. 25, No. 1, pp. 13-22.

* cited by examiner

*Primary Examiner* — Emily A Bernhardt
*Assistant Examiner* — Laura M Daniel
(74) *Attorney, Agent, or Firm* — Hoyng Rokh Monegier LLP; David P. Owen

(57) ABSTRACT

The present invention relates to compounds for prophylaxis or treatment of organ damage by restoring endothelial function and/or inhibiting reactive oxygen species production and especially to compounds for prophylaxis or treatment of diabetic kidney damage. Specifically, the present invention relates to 6-hydroxy-2,5,7,8-tetramethylchroman-2-yl)(piperazin-1-yl)methanone or N,6-dihydroxy-2,5,7,8-tetramethylchroman-2-carboxamide or a pharmaceutically acceptable salt or base thereof for use in the prophylaxis or treatment of organ damage by restoring endothelial function and/or inhibiting reactive oxygen species production and especially diabetic kidney organ damage.

2 Claims, 7 Drawing Sheets

COMPOUND FOR THE PROPHYLAXIS OR TREATMENT OF ORGAN DAMAGE

CROSS REFERENCE TO RELATED APPLICATIONS

This application is a 371 of PCT application number PCT/EP2016/060731 filed on May 12, 2016, which claims priority from NL application number 2014843 filed on May 22, 2015. Both applications are hereby incorporated by reference in their entireties.

The present invention relates to compounds for prophylaxis or treatment of organ damage by restoring endothelial function and/or inhibiting reactive oxygen species production and especially to compounds for prophylaxis or treatment of diabetic kidney damage.

Diabetic nephropathy (nephropatia diabetica), also known as nodular diabetic glomerulosclerosis or intercapillary glomerulonephritis, is a progressive kidney disease caused by angiopathy of capillaries in the kidney glomeruli. It is characterized by nephrotic syndrome and diffuse glomerulosclerosis. Diabetic nephropathy is generally caused by longstanding diabetes mellitus, and is a prime indication for dialysis in many developed countries.

Kidney failure provoked by glomerulosclerosis leads to fluid filtration deficits and other disorders of kidney function. There is an increase in blood pressure (hypertension) and fluid retention in the body plus a reduced plasma oncotic pressure causing edema. Other complications may be arteriosclerosis of the renal artery and protein in the urine.

The first laboratory abnormality generally is a positive microalbuminuria test. The diagnosis Diabetic nephropathy is suspected when a routine urinalysis of a person with diabetes shows too much protein in the urine (proteinuria). The urinalysis may also show glucose in the urine, especially if blood glucose is poorly controlled. Serum creatinine and BUN may increase as kidney damage progresses. A kidney biopsy generally confirms the diagnosis, although it is not always necessary if the case is straightforward with a documented progression of proteinuria over time and presence of diabetic retinopathy on examination of the retina of the eyes.

Glomerular hyperfiltration is the basic pathophysiology in diabetic nephropathy leading to intraglomerular hypertension. ACE inhibitor drugs help prevent diabetic nephropathy by preventing this step. Progression from glomerular hyperfilteration leads to the stage of basement membrane thickening. This is the earliest detectable change in the course of diabetic nephropathy. This is followed by expansion of mesangium and finally by nodular sclerosis. At this stage, the kidney may leak more serum albumin (plasma protein) than normal in the urine (albuminuria), and this can be detected by medical tests for albumin. As diabetic nephropathy progresses, increasing numbers of glomeruli are destroyed by progressive nodular glomerulosclerosis. A kidney biopsy generally clearly shows diabetic nephropathy. Diabetic nephropathy is usually preceded by the onset of diabetic retinopathy; the evidence of nephropathy without retinopathy gives the suspicion that the renal impairment is not caused by diabetes itself but it is the result of comorbidity (e.g. glomerulonephritis).

The goals of treatment of Diabetic nephropathy are to slow the progression of kidney damage and control related complications. The main treatment, once proteinuria is established, is using ACE inhibitor drugs, which usually reduces proteinuria levels and slows the progression of diabetic nephropathy. Several effects of the ACEIs that may contribute to renal protection have been related to the association of rise in Kinins which is also responsible for some of the side effects associated with ACEIs therapy such as dry cough. The renal protection effect is related to the antihypertensive effects in normal and hypertensive patients, renal vasodilatation resulting in increased renal blood flow and dilatation of the efferent arterioles. Many studies have shown that related drugs, angiotensin receptor blockers (ARBs), have a similar benefit.

Several compounds are in development for diabetic nephropathy. These compounds include bardoxolone methyl, olmesartan medoxomil, sulodexide, NOX-E36, and avosentan.

However, despite the above, there remains a continuous need in the art for further compounds for the prophylaxis or treatment of diabetic nephropathy or diabetic kidney disease.

It is an object of the present invention, amongst other objects, to meet the above need in the art.

According to the present invention, the above object, amongst other objects, is met by providing compounds as outlined in the appended claims.

Specifically, the above object, amongst other objects, is met by the present invention by a compound according to formula (I), or a pharmaceutically acceptable salt or base thereof, for use in the prophylaxis or treatment of organ damage by restoring endothelial function and/or inhibiting reactive oxygen species production, preferably wherein said wherein said organ damage is diabetic organ damage and/or said organ is kidney,

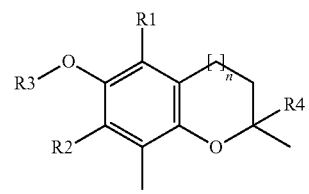

I wherein R1 and R2 may be the same or different, and represent a C1-C4 linear or branched alkyl group;

wherein R3 represents a hydrogen or prodrug moiety that can be removed in living tissue; preferably, R3 forms together with the 6-oxygen an ester group. R3 may have 1-12 carbon atoms, preferably 1-6 carbon atoms, and may comprise one or more amine or oxygen atoms;

n may be 0 or 1, and is preferably 1;

R4 is a group comprising at 1-20 carbon atoms and at least one nitrogen atom; R4 may comprise further nitrogen atoms, one or more oxygen atoms, halogen, sulphur or phosphor atoms and R4 may comprise aromatic groups, wherein the molecular weight of R4 preferably is less than 300 Da.

As will be recognized, the compound of formula (I) is derived from trolox, a water soluble analogue of vitamin E. In trolox, R1 and R2 are methyl, R3 is hydrogen, and R4 is carboxylic acid.

Specifically, the above object, amongst other objects, is met by the present invention by a compound according to the formula (II)

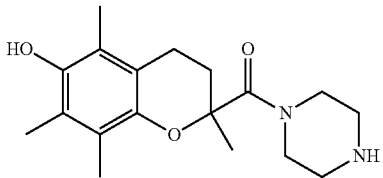 [SMILES: Cc1c(C)c2c(c(C)c1O)CCC(C)(C(=O)N1CCNCC1)O2]

(6-hydroxy-2,5,7,8-tetramethylchroman-2-yl)(piperazin-1-yl)methanone (II)

or a pharmaceutically acceptable salt or base thereof for use in the prophylaxis or treatment of organ damage by restoring endothelial function and/or inhibiting reactive oxygen species production, preferably wherein said wherein said organ damage is diabetic organ damage and/or said organ is kidney.

According to the present invention, according to a further aspect, the above object, amongst other objects, are met by a compound according to the formula (III)

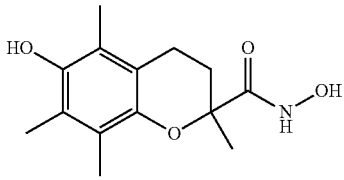 [SMILES: Cc1c(C)c2c(c(C)c1O)CCC(C)(C(=O)NO)O2]

N,6-dihydroxy-2,5,7,8-tetramethylchroman-2-carboxamide (III)

or a pharmaceutically acceptable salt or base thereof for use in the prophylaxis or treatment of organ damage by restoring endothelial function and/or inhibiting reactive oxygen species production, preferably wherein said wherein said organ damage is diabetic organ damage and/or said organ is kidney.

According to the present invention, according to a further aspect, the above object, amongst other objects, are met by a compound selected from the group, together "group A", consisting of 2,2,5,7,8-pentamethylchroman-6-ol; (S)-6-hydroxy-2,5,7,8-tetramethylchroman-2-carboxylic acid; (R)-6-hydroxy-2,5,7,8-tetramethylchroman-2-carboxylic acid; 6-hydroxy-2,5,7,8-tetramethylchroman-2-carboxamide; N-butyl-6-hydroxy-2,5,7,8-tetramethylchroman-2-carboxamide; 6-hydroxy-N-isopropyl-2,5,7,8-tetramethylchroman-2-carboxamide; (E)-N-(3,7-dimethylocta-2,6-dien-1-yl)-6-hydroxy-2,5,7,8-tetramethylchroman-2-carboxamide; (6-hydroxy-2,5,7,8-tetramethylchroman-2-yl)(morpholino)methanone; N-(4-fluorobenzyl)-6-hydroxy-2,5,7,8-tetramethylchroman-2-carboxamide; 6-hydroxy-N—((S)-2-hydroxy-1-phenylethyl)-2,5,7,8-tetramethylchroman-2-carboxamide; 6-hydroxy-2,5,7,8-tetramethyl-N-(2-(methylamino)ethyl)chroman-2-carboxamide; 6-hydroxy-N,2,5,7,8-pentamethyl-N-(2-(methylamino)ethyl)chroman-2-carboxamide; 6-hydroxy-2,5,7,8-tetramethyl-N-(3-(piperidin-1-yl)propyl)chroman-2-carboxamide; 6-hydroxy-2,5,7,8-tetramethyl-N-(3-nitrophenyl)chroman-2-carboxamide; N-(4-fluorophenyl)-6-hydroxy-2,5,7,8-tetramethylchroman-2-carboxamide; methyl 4-(6-hydroxy-2,5,7,8-tetramethylchroman-2-carboxamido)benzoate; (4-butylpiperazin-1-yl)(6-hydroxy-2,5,7,8-tetramethylchroman-2-yl)methanone; (6-hydroxy-2,5,7,8-tetramethylchroman-2-yl)(4-(2-hydroxyethyl)piperazin-1-yl)methanone; ((2S,5R)-4-allyl-2,5-dimethylpiperazin-1-yl)(6-hydroxy-2,5,7,8-tetramethylchroman-2-yl)methanone; N—((R)-2-amino-2-oxo-1-phenylethyl)-6-hydroxy-2,5,7,8-tetramethylchroman-2-carboxamide; (6-hydroxy-2,5,7,8-tetramethylchroman-2-yl)((S)-2-(hydroxymethyl)pyrrolidin-1-yl)methanone; N-(2-bromoethyl)-6-hydroxy-2,5,7,8-tetramethylchroman-2-carboxamide; N'-(2-cyanoethyl)-6-hydroxy-2,5,7,8-tetramethylchroman-2-carbohydrazide; 2-(((4-fluorobenzyl)amino)methyl)-2,5,7,8-tetramethylchroman-6-ol; 2-((butylamino)methyl)-2,5,7,8-tetramethylchroman-6-ol; 6-hydroxy-5,7-diisopropyl-2,8-dimethylchroman-2-carboxylic acid; 2-(hydroxymethyl)-5,7-diisopropyl-2,8-dimethylchroman-6-ol; 6-hydroxy-N—((R)-1-hydroxypropan-2-yl)-2,5,7,8-tetramethylchroman-2-carboxamide; (6-hydroxy-2,5,7,8-tetramethylchroman-2-yl)(4-(2-(2-hydroxyethoxy)ethyl)piperazin-1-yl)methanone; N-(2-cyanoethyl)-6-hydroxy-2,5,7,8-tetramethylchroman-2-carboxamide; 6-hydroxy-N-(2-((2-hydroxyethyl)(methyl)amino)ethyl)-2,5,7,8-tetramethylchroman-2-carboxamide; (R)—N,6-dihydroxy-2,5,7,8-tetramethylchroman-2-carboxamide; (S)—N,6-dihydroxy-2,5,7,8-tetramethylchroman-2-carboxamide; 2-(((S)-2-(hydroxymethyl)pyrrolidin-1-yl)methyl)-2,5,7,8-tetramethylchroman-6-ol; 2-((((S)-2-hydroxy-1-phenylethyl)amino)methyl)-2,5,7,8-tetramethylchroman-6-ol; 2,5,7,8-tetramethyl-2-(piperidin-1-ylmethyl)chroman-6-ol; N,6-dihydroxy-5,7-diisopropyl-2,8-dimethylchroman-2-carboxamide; (6-hydroxy-2,5,7,8-tetramethylchroman-2-yl)(4-(2-hydroxyethyl)piperazin-1-yl)methanone; (6-hydroxy-5,7-diisopropyl-2,8-dimethylchroman-2-yl)(4-(2-hydroxyethyl)piperazin-1-yl)methanone; 2-(((S)-2-(hydroxymethyl)pyrrolidin-1-yl)methyl)-2,5,7,8-tetramethylchroman-6-ol; 2-(((S)-2-(hydroxymethyl)pyrrolidin-1-yl)methyl)-2,5,7,8-tetramethylchroman-6-ol; 2-(4-(6-hydroxy-2,5,7,8-tetramethylchroman-2-carbonyl)piperazin-1-yl)acetic acid; (6-hydroxy-5,7-diisopropyl-2,8-dimethylchroman-2-yl)(piperazin-1-yl)methanone; (6-hydroxy-2,5,7,8-tetramethylchroman-2-yl)(4-(2-hydroxyethyl)piperazin-1-yl)methanone; 2-(4-(6-hydroxy-5,7-diisopropyl-2,8-dimethylchroman-2-carbonyl)piperazin-1-yl)acetic acid; ethyl 2-(4-(6-hydroxy-2,5,7,8-tetramethylchroman-2-carbonyl)piperazin-1-yl)acetate; (S)-2-(4-(6-hydroxy-2,5,7,8-tetramethylchroman-2-carbonyl)piperazin-1-yl)acetic acid; (R)-2-(4-(6-hydroxy-2,5,7,8-tetramethylchroman-2-carbonyl)piperazin-1-yl)acetic acid; (2S)-1-(6-hydroxy-2,5,7,8-tetramethylchroman-2-carbonyl)pyrrolidine-2-carboxylic acid; (2S)-1-(6-hydroxy-2,5,7,8-tetramethylchroman-2-carbonyl)pyrrolidine-2-carboxylic acid; (2S)-1-(6-hydroxy-2,5,7,8-tetramethylchroman-2-carbonyl)pyrrolidine-2-carboxylic acid and pharmaceutically acceptable salts or bases thereof for use in the prophylaxis or treatment of organ damage by restoring endothelial function and/or inhibiting reactive oxygen species production, preferably wherein said wherein said organ damage is diabetic organ damage and/or said organ is kidney.

The present inventors surprisingly discovered that the present compounds according to formula (I), and most preferably (6-hydroxy-2,5,7,8-tetramethylchroman-2-yl)(piperazin-1-yl)methanone or N,6-dihydroxy-2,5,7,8-tetramethylchroman-2-carboxamide have a significant effect on restoring endothelial function and/or inhibiting reactive oxygen species in a mouse model of diabetes making them suitable for in the prophylaxis or treatment of organ damage by restoring endothelial function and/or inhibiting reactive oxygen species production in organs and especially in diabetic nephropathy or diabetic kidney disease.

According to a preferred embodiment of the present invention, the present prophylaxis or treatment comprises administration of the present compounds such as the compounds according formula (I), (II), and (III), or according to group A in a therapeutically effective dose.

The compound according to formula (I),

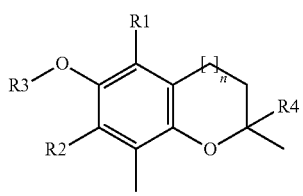

preferably has the following characteristics:

R1 and R2 may be the same or different, and represent a C1-C4 linear or branched alkyl group. Preferably, R1 and R2 are methyl, ethyl or isopropyl, and most preferably, R1 and R3 are the same, and are methyl or isopropyl. Other suitable groups are n-butyl and t-butyl.

R3 represents a hydrogen or prodrug moiety that can be removed in living tissue. Preferably, R3 forms together with the 6-oxygen an ester group. R3 may have 1-12 carbon atoms, preferably 1-6 carbon atoms, and may comprise one or more amine or oxygen atoms. Suitable groups—together with the 6-oxygen—include ethyl-ester, butyl-ester, benzoyl-ester, or an ester of an amino-acid, or amino acids wherein the amino group is amidated with an alkyl carboxylic acid having 1-4 carbon atoms. In one preferred embodiment, R3 is hydrogen.

n may be 0 or 1, and is preferably 1;

R4 is a group comprising at 1-20 carbon atoms and at least one nitrogen atom. R4 may comprise further nitrogen atoms, one or more oxygen atoms, halogen, sulphur or phosphor atoms and R4 may comprise aromatic groups.

The molecular weight of R4 preferably is less than 300 Da.

Preferably, the compound according to formula (I) has a molecular weight lower than 500 Da.

Preferably, the compound according to formula (I) does not comprise an aromatic heterocyclic ring.

Preferably, R4 comprises a carbonyl group, and most preferably, a carbonyl group attached to the trolox moiety.

In one preferred embodiment, R4 is —CO—N—R5, wherein the C=O is bound to the trolox moiety, and wherein R5 is an alkyl group, optionally substituted with nitrogen or oxygen, wherein the alkyl group comprises 1-12 carbon atoms, and wherein nitrogen can be amine, quaternary amine, guanidine or imine, and oxygen can be hydroxyl, carbonyl or carboxylic acid. Oxygen and nitrogen together may form amide, urea or carbamate groups.

The alkyl group in R5 may be linear, branched or cyclic, and preferably comprises at least one cyclic structure.

Compounds as presented by formula (I) can be made according to known chemical synthesis.

For example, compounds with a guanidine group, or a piperazine group attached to a trolox moiety via an alkyl group are described in EP202580. Analogous synthesis can be used, wherein the 6-oxygen is protected, and liberated after the synthesis, or protected with a prodrug-moiety.

For example, compounds with nicotinate groups as substituents, are described in US461890. The nicotinate attached to the 6-oxygen of the trolox moiety can act as a prodrug moiety, which is hydrolysed in vivo to a free hydroxyl group.

For example, suitable compounds are described in WO88/08424, examples 18-23 and 78-164.

For example, suitable compounds are described in WO97/41121, in preparations 1, 6, 7, 12-15, 21, 24 and 27, wherein the benzoyl group can be removed, or can act as a prodrug moiety.

Further compounds are described in e.g. WO03/024943, like compounds 9-11, 25-28, 109-112, 119-122 etc.

For example, compounds having a quaternary ammonium group are described in WO2014/011047, including a description of synthesis in the examples.

The present invention will be further detailed in the examples below. In the examples, reference is made to figures wherein:

FIG. 1 shows metabolic data of SUL121 treated diabetic and non-diabetic mice. A) body weight, B) Water intake, C) Urine output, D) Non fasting plasma glucose levels. E) Blood pressure. *$p<0.05$ diabetic SUL121 vs diabetic control;

EXAMPLES

Example 1: Synthesis of Several Compounds

Figure 1:
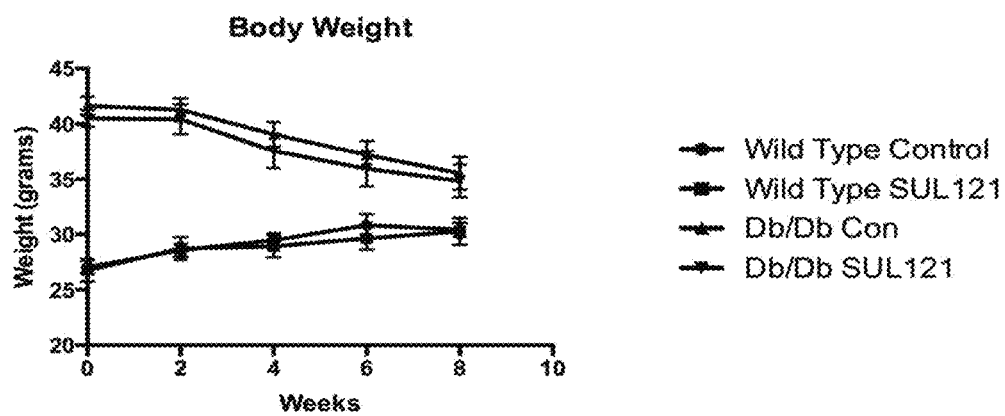
Figure 1:
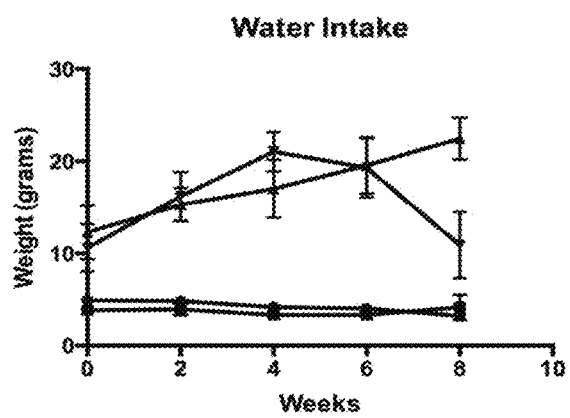
Figure 1:
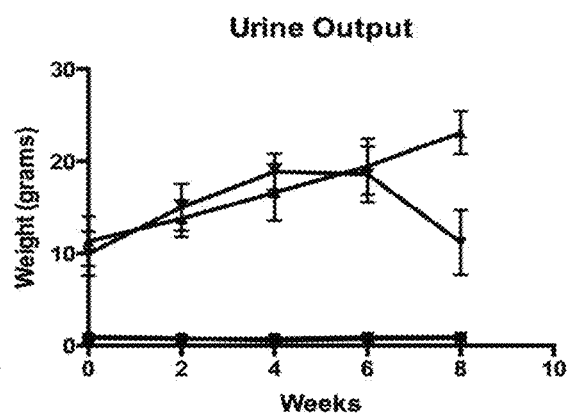
Figure 1:
Figure 1:
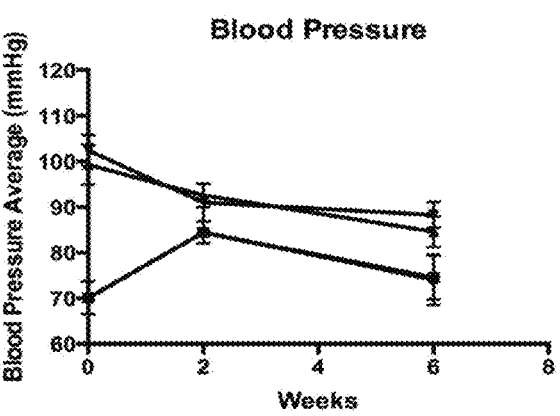

Compounds according to the invention can be synthesized according to standard synthesis methods which are well known by a person skilled in the art. SUL-0083, SUL-0084 and SUL-0085 are commercially available. Table 1 below provides a summary of the present compounds as an interchangeable arbitrary indication (code) of the present compounds used herein.

TABLE 1

Several compounds according to the present invention

| Code | Chemical name |
|---|---|
| SUL-083 | 2,2,5,7,8-pentamethylchroman-6-ol |
| SUL-084 | (S)-6-hydroxy-2,5,7,8-tetramethylchroman-2-carboxylic acid |
| SUL-085 | (R)-6-hydroxy-2,5,7,8-tetramethylchroman-2-carboxylic acid |
| SUL-089 | 6-hydroxy-2,5,7,8-tetramethylchroman-2-carboxamide |
| SUL-090 | N,6-dihydroxy-2,5,7,8-tetramethylchroman-2-carboxamide; |
| SUL-091 | N-butyl-6-hydroxy-2,5,7,8-tetramethylchroman-2-carboxamide; |
| SUL-092 | 6-hydroxy-N-isopropyl-2,5,7,8-tetramethylchroman-2-carboxamide; |
| SUL-093 | (E)-N-(3,7-dimethylocta-2,6-dien-1-yl)-6-hydroxy-2,5,7,8-tetramethylchroman-2-carboxamide; |
| SUL-095 | (6-hydroxy-2,5,7,8-tetramethylchroman-2-yl)(morpholino)methanone; |
| SUL-097 | N-(4-fluorobenzyl)-6-hydroxy-2,5,7,8-tetramethylchroman-2-carboxamide; |
| SUL-098 | 6-hydroxy-N-((S)-2-hydroxy-1-phenylethyl)-2,5,7,8-tetramethylchroman-2-carboxamide; |
| SUL-100 | 6-hydroxy-2,5,7,8-tetramethyl-N-(2-(methylamino)ethyl)chroman-2-carboxamide; |
| SUL-101 | 6-hydroxy-N,2,5,7,8-pentamethyl-N-(2-(methylamino)ethyl)chroman-2-carboxamide; |
| SUL-102 | 6-hydroxy-2,5,7,8-tetramethyl-N-(3-(piperidin-1-yl)propyl)chroman-2-carboxamide; |
| SUL-104 | 6-hydroxy-2,5,7,8-tetramethyl-N-(3-nitrophenyl)chroman-2-carboxamide; |
| SUL-106 | N-(4-fluorophenyl)-6-hydroxy-2,5,7,8-tetramethylchroman-2-carboxamide; |
| SUL-107 | methyl 4-(6-hydroxy-2,5,7,8-tetramethylchroman-2-carboxamido)benzoate; |
| SUL-108 | (4-butylpiperazin-1-yl)(6-hydroxy-2,5,7,8-tetramethylchroman-2-yl)methanone; |
| SUL-109 | (6-hydroxy-2,5,7,8-tetramethylchroman-2-yl)(4-(2-hydroxyethyl)piperazin-1-yl)methanone; |
| SUL-110 | ((2S,5R)-4-allyl-2,5-dimethylpiperazin-1-yl)(6-hydroxy-2,5,7,8-tetramethylchroman-2-yl)methanone; |
| SUL-111 | N-((R)-2-amino-2-oxo-1-phenylethyl)-6-hydroxy-2,5,7,8-tetramethylchroman-2-carboxamide; |
| SUL-112 | (6-hydroxy-2,5,7,8-tetramethylchroman-2-yl)((S)-2-(hydroxymethyl)pyrrolidin-1-yl)methanone; |
| SUL-114 | N-(2-bromoethyl)-6-hydroxy-2,5,7,8-tetramethylchroman-2-carboxamide; |
| SUL-115 | N'-(2-cyanoethyl)-6-hydroxy-2,5,7,8-tetramethylchroman-2-carbohydrazide; |
| SUL-116 | 2-(((4-fluorobenzyl)amino)methyl)-2,5,7,8-tetramethylchroman-6-ol; |
| SUL-117 | 2-((butylamino)methyl)-2,5,7,8-tetramethylchroman-6-ol; |
| SUL-118 | 6-hydroxy-5,7-diisopropyl-2,8-dimethylchroman-2-carboxylic acid; |
| SUL-119 | 2-(hydroxymethyl)-5,7-diisopropyl-2,8-dimethylchroman-6-ol; |
| SUL-120 | 6-hydroxy-N-((R)-1-hydroxypropan-2-yl)-2,5,7,8-tetramethylchroman-2-carboxamide |
| SUL-121 | (6-hydroxy-2,5,7,8-tetramethylchroman-2-yl)(piperazin-1-yl)methanone |
| SUL-122 | (6-hydroxy-2,5,7,8-tetramethylchroman-2-yl)(4-(2-(2-hydroxyethoxy)ethyl)piperazin-1-yl)methanone; |
| SUL-123 | N-(2-cyanoethyl)-6-hydroxy-2,5,7,8-tetramethylchroman-2-carboxamide; |
| SUL-124 | 6-hydroxy-N-(2-((2-hydroxyethyl)(methyl)amino)ethyl)-2,5,7,8-tetramethylchroman-2-carboxamide; |
| SUL-125 | (R)-N,6-dihydroxy-2,5,7,8-tetramethylchroman-2-carboxamide; |
| SUL-126 | (S)-N,6-dihydroxy-2,5,7,8-tetramethylchroman-2-carboxamide; |
| SUL-128 | 2-(((S)-2-(hydroxymethyl)pyrrolidin-1-yl)methyl)-2,5,7,8-tetramethylchroman-6-ol; |
| SUL-129 | 2-((((S)-2-hydroxy-1-phenylethyl)amino)methyl)-2,5,7,8-tetramethylchroman-6-ol; |
| SUL-130 | 2,5,7,8-tetramethyl-2-(piperidin-1-ylmethyl)chroman-6-ol; |
| SUL-131 | N,6-dihydroxy-5,7-diisopropyl-2,8-dimethylchroman-2-carboxamide; |
| SUL-132 | (6-hydroxy-2,5,7,8-tetramethylchroman-2-yl)(4-(2-hydroxyethyl)piperazin-1-yl)methanone; |
| SUL-133 | (6-hydroxy-5,7-diisopropyl-2,8-dimethylchroman-2-yl)(4-(2-hydroxyethyl)piperazin-1-yl)methanone; |
| SUL-134 | 2-((S)-2-(hydroxymethyl)pyrrolidin-1-yl)methyl)-2,5,7,8-tetramethylchroman-6-ol; |
| SUL-135 | 2-(((S)-2-(hydroxymethyl)pyrrolidin-1-yl)methyl)-2,5,7,8-tetramethylchroman-6-ol; |
| SUL-136 | 2-(4-(6-hydroxy-2,5,7,8-tetramethylchroman-2-carbonyl)piperazin-1-yl)acetic acid; |
| SUL-137 | (6-hydroxy-5,7-diisopropyl-2,8-dimethylchroman-2-yl)(piperazin-1-yl)methanone; |
| SUL 138 | (6-hydroxy-2,5,7,8-tetramethylchroman-2-yl)(4-(2-hydroxyethyl)piperazin-1-yl)methanone; |
| SUL-139 | 2-(4-(6-hydroxy-5,7-diisopropyl-2,8-dimethylchroman-2-carbonyl)piperazin-1-yl)acetic acid; |
| SUL-140 | ethyl 2-(4-(6-hydroxy-2,5,7,8-tetramethylchroman-2-carbonyl)piperazin-1-yl)acetate; |
| SUL-141 | (S)-2-(4-(6-hydroxy-2,5,7,8-tetramethylchroman-2-carbonyl)piperazin-1-yl)acetic acid; |
| SUL-142 | (R)-2-(4-(6-hydroxy-2,5,7,8-tetramethylchroman-2-carbonyl)piperazin-1-yl)acetic acid; |

TABLE 1-continued

Several compounds according to the present invention

| Code | Chemical name |
|---|---|
| SUL-143 | (2S)-1-(6-hydroxy-2,5,7,8-tetramethylchroman-2-carbonyl)pyrrolidine-2-carboxylic acid; |
| SUL-144 | (2S)-1-(6-hydroxy-2,5,7,8-tetramethylchroman-2-carbonyl)pyrrolidine-2-carboxylic acid; |
| SUL-145 | (2S)-1-(6-hydroxy-2,5,7,8-tetramethylchroman-2-carbonyl)pyrrolidine-2-carboxylic acid; |

Synthesis of SUL 089-112, 114-117, 120-126, 128-130, 132, 134-135, 138, and 140

Amidation of trolox was achieved by reaction with the appropriate amine in the presence of standard coupling reagents for amide formation, e.g., HATU and CDI. The corresponding amines were prepared by reduction of the amides formed with $BH_3$. Hydroxamic acid derivatives were prepared by reaction with hydroxylamine/CDI. The synthesis of carbohydrazide analogues of trolox was achieved by reaction with (substituted) hydrazines. Enantiomeric/diastereomeric compounds were prepared starting from enantiomerically pure (R)- or (S)-Trolox or by means of chiral chromatography.

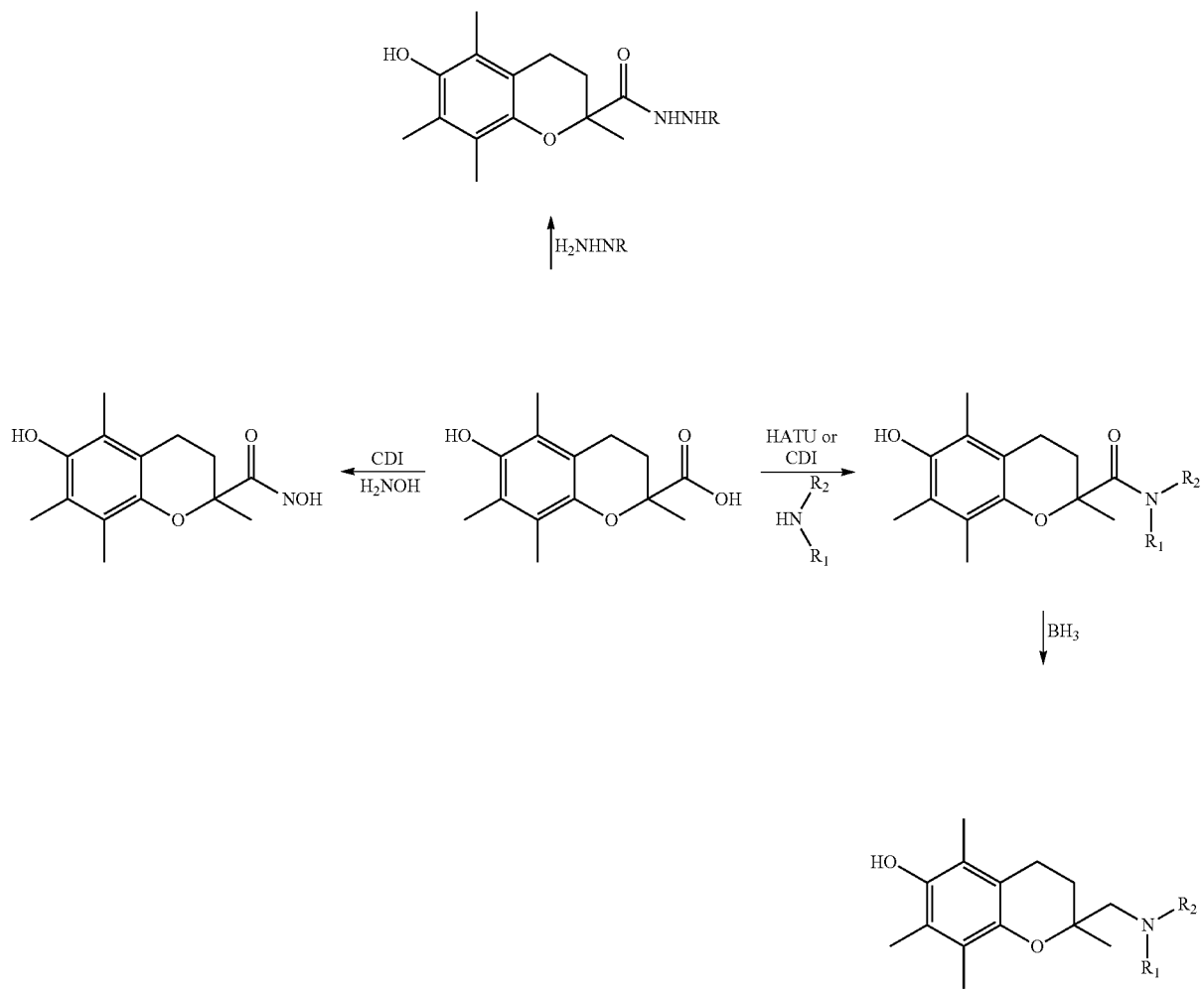

Synthesis of SUL-118, SUL-119 en SUL-146

Oxidation of commercially available propofol with salcomine, a coordination complex of the salen ligand with cobalt, followed by reduction with NaBH$_4$ afforded 2,6-diisopropylbenzene-1,4-diol Subsequent methylation with HCO/SnCl$_2$/HCl and reaction with methyl methacrylate furnished SUL-146 (methyl 6-hydroxy-5,7-diisopropyl-2,8-dimethylchroman-2-carboxylate). Hydrolysis with LiOH yielded the carboxylic acid SUL-118 (6-hydroxy-5,7-diisopropyl-2,8-dimethylchroman-2-carboxylic acid). The alcohol SUL-119 (2-(hydroxymethyl)-5,7-diisopropyl-2,8-dimethylchroman-6-ol) was obtained by reduction of SUL-146 with LiAlH$_4$.

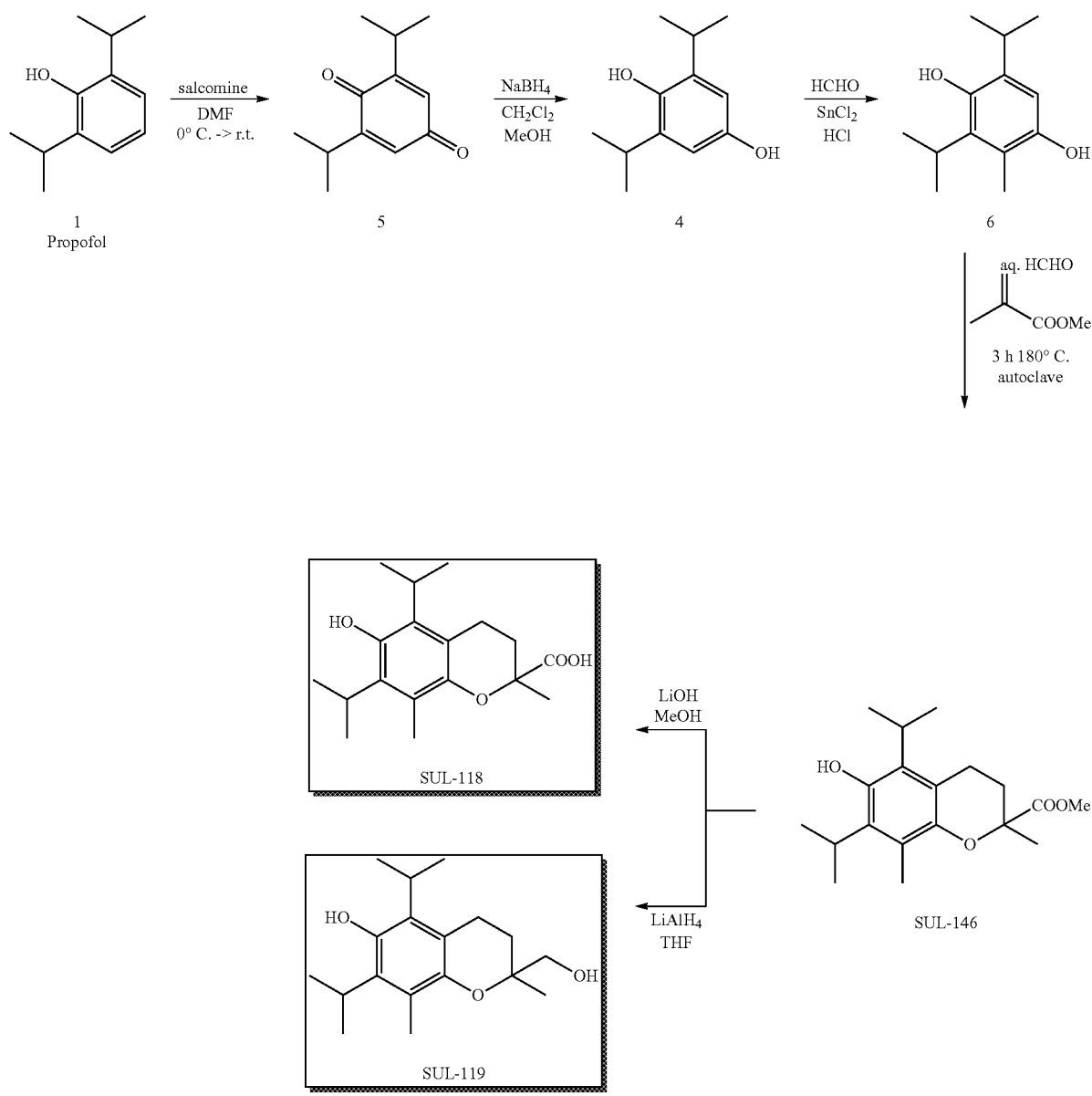

Synthesis of SUL-131, SUL-133, SUL 137 en SUL-146

Starting from the carboxylic acid SUL-118 (6-hydroxy-5,7-diisopropyl-2,8-dimethylchroman-2-carboxylic acid), the hydroxylamine was obtained by reaction with hydroxylamine using CDI as coupling reagent. Compounds SUL 133 ((6-hydroxy-5,7-diisopropyl-2,8-dimethylchroman-2-yl)(4-(2-hydroxyethyl)piperazin-1-yl)methanone) and SUL 137 ((6-hydroxy-5,7-diisopropyl-2,8-dimethylchroman-2-yl)(piperazin-1-yl)methanone) were prepared by reaction of SUL-118 with the appropriate piperazine derivative. Both coupling reagents HATU and CDI resulted in satisfactorily yields. SUL 139 (2-(4-(6-hydroxy-5,7-diisopropyl-2,8-dimethylchroman-2-carbonyl)piperazin-1-yl)acetic acid) was prepared by a reductive amination of SUL 137 ((6-hydroxy-5,7-diisopropyl-2,8-dimethylchroman-2-yl)(piperazin-1-yl)methanone) with glyoxalic acid.

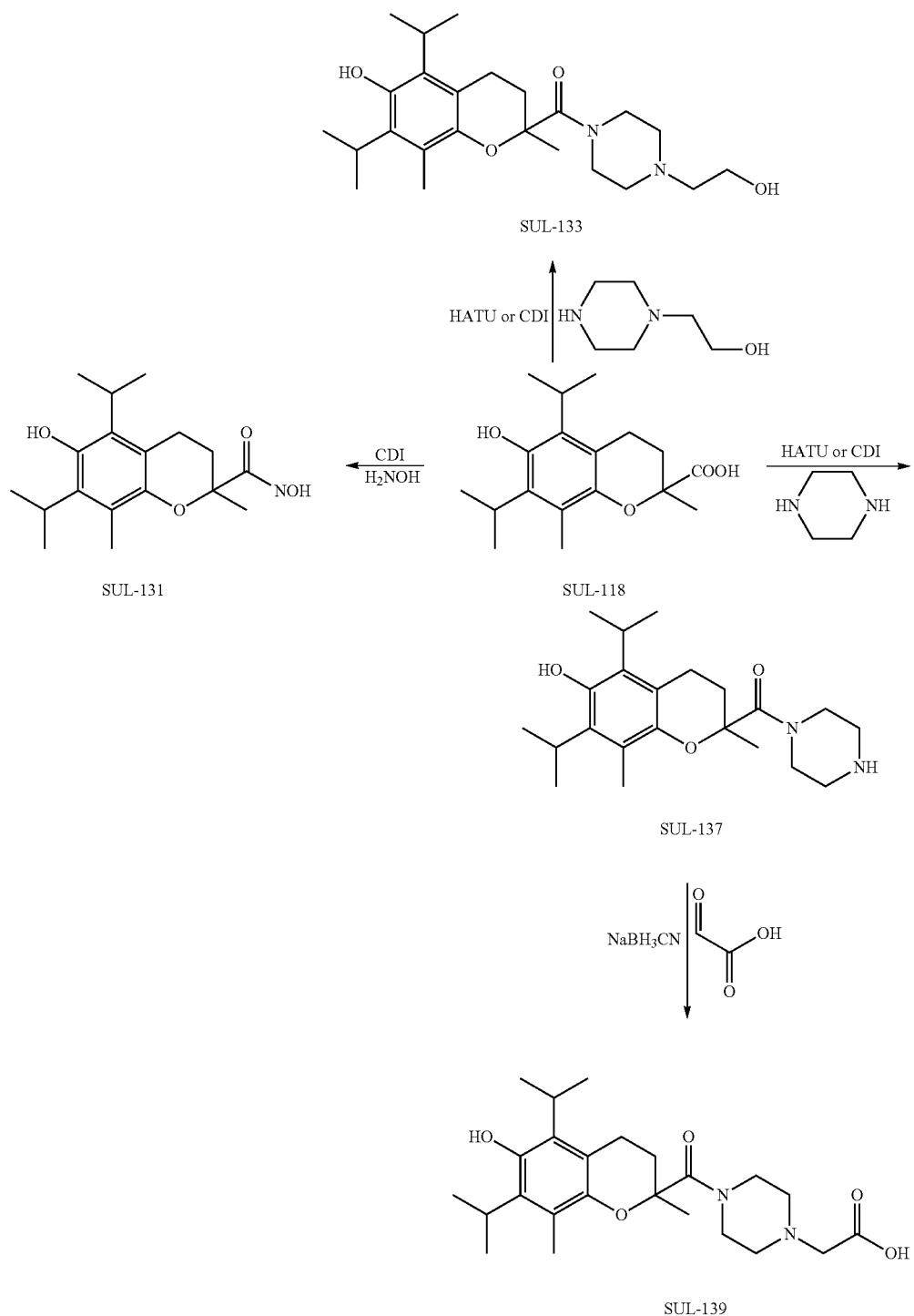

Synthesis of SUL-136, SUL-141 and SUL-142

Hydrolysis of SUL-140 (ethyl 2-(4-(6-hydroxy-2,5,7,8-tetramethylchroman-2-carbonyl)piperazin-1-yl)acetate) under N₂ atmosphere furnished SUL-136 (2-(4-(6-hydroxy-2,5,7,8-tetramethylchroman-2-carbonyl)piperazin-1-yl)acetic acid) in high yield. The enantiomers SUL-141 and SUL-142 were prepared according to the above-described conditions.

2-carbonyl)pyrrolidine-2-carboxylic acid, diastereomer 2). The racemic analogue SUL-143 ((2S)-1-(6-hydroxy-2,5,7,8-tetramethylchroman-2-carbonyl)pyrrolidine-2-carboxylic acid) was obtained by mixing the esters of the individual diastereoisomers followed by hydrolysis of the ester moiety using LiOH.

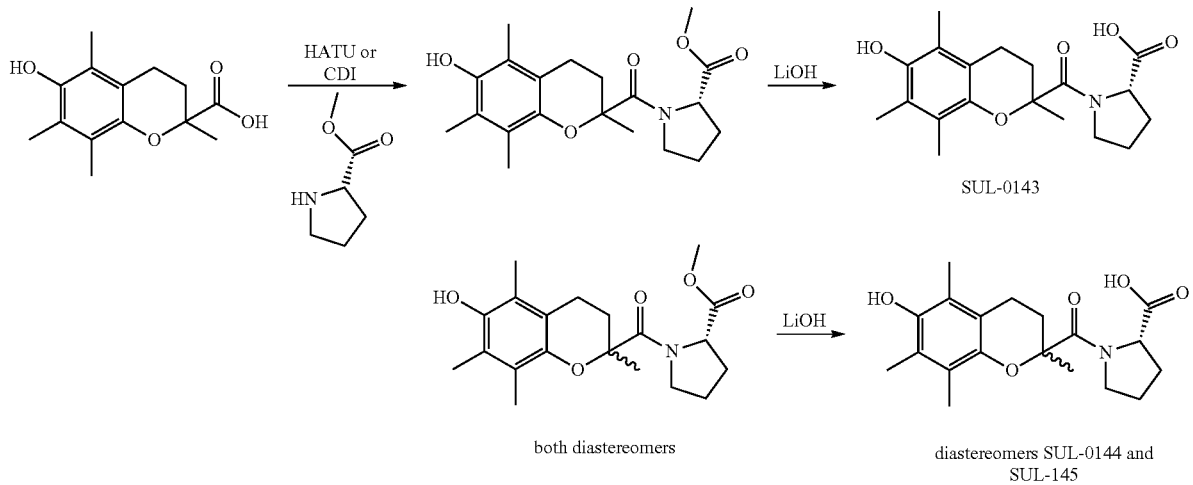

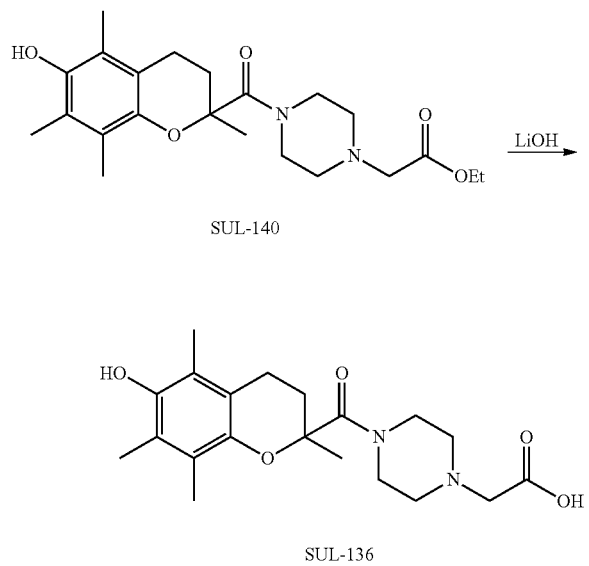

Synthesis of SUL 143, 144 en 145

Amidation of trolox with (S)-methyl pyrrolidine-2-carboxylate (L-proline methyl ester) afforded, after column chromatography, two diastereoisomers. Subsequent hydrolysis of the individual diastereoisomers afforded SUL-144 ((2S)-1-(6-hydroxy-2,5,7,8-tetramethylchroman-2-carbonyl)pyrrolidine-2-carboxylic acid, diastereomer 1) and SUL-145 ((2S)-1-(6-hydroxy-2,5,7,8-tetramethylchroman-

Amidation of Trolox (General Example)

SUL-108 ((4-butylpiperazin-1-yl)(6-hydroxy-2,5,7,8-tetramethylchroman-2-yl)methanone). HCl Trolox (11 g, 0.044 mol, 1 eq.) was suspended in acetonitrile (100-150 ml). CDI (8.6 g, 0.053 mol, 1.2 eq.) was added in portions. The reaction mixture was stirred for 0.5-1 hour at room temperature. After addition of 1-butylpiperazine (6.9 g, 0.048 mol, 1.1 eq.) the reaction mixture was stirred at 25-30° C. over the weekend. The reaction mixture was concentrated, H₂O (200 ml) was added and the aqueous layer was extracted with EtOAc (4×). The combined organic layers were dried, filtered and concentrated. The crude product obtained was purified by column chromatography (DCM/10% MeOH) affording the compound aimed for (9 g product, 82% pure). Crystallization from EtOAc/heptanes afforded SUL-108 (6 g, 0.016 mol, 36% yield, 90% pure) as a white solid. The material obtained was dissolved in DCM (50-100 ml). HCl (4 M in dioxane, 8.8 ml, 0.0035 mol, 2.2 eq.) was added and the reaction mixture was stirred at room temperature over the weekend. The mixture was filtered, rinsed with DCM, and dried to afford the HCl salt of SUL-108 (6.3 g, 97-98% pure) as a white solid.

$^1$H-NMR (CDCl₃, in ppm): 0.93 (t, 3H), 1.38 (m, 2H), 1.58 (s, 3H), 1.67 (m, 2H), 2.09 (s, 3H), 2.12 (s, 3H), 2.15 (s, 3H), 2.50-3.20 (m, 14H). M$^+$=375.3

Reduction of Trolox Amides (General Example)

SUL-128. (2-(((S)-2-(hydroxymethyl)pyrrolidin-1-yl)methyl)-2,5,7,8-tetramethylchroman-6-ol).HCl BH₃.THF in THF (16 ml, 0.0156 mol, 2 eq.) was cooled to T=0° C. A solution of SUL-112 ((6-hydroxy-2,5,7,8-tetramethylchroman-2-yl)((S)-2-(hydroxymethyl)pyrrolidin-1-yl)methanone; 2.6 g, 0.0078 mol, 1 eq.) in THF (50 ml) was added drop-wise and the reaction mixture was refluxed for 1 hour and cooled to room temperature overnight. The reaction mixture was cooled on an ice bath and HCl (6 M, 25 ml) was added drop-wise. DCM (100 ml) was added and the layers were separated. The aqueous layer was extracted with DCM (3×). The combined org. layers were dried over $K_2CO_3$ until no gas formation was noticed anymore. The organic phase was filtered and concentrated. The crude product was cooled on an ice bath, and NaOH (6M, 50 ml) was added drop-wise. After addition the reaction mixture was stirred for 1 hour and extracted with DCM (4×). The combined DCM layers were dried, filtered and concentrated to give 1.6 g crude product (20-40% pure). The material was purified by column chromatography affording SUL-128 (300 mg, 0.94 mmol, 12% yield, 90% pure). This was dissolved in DCM (10 ml) and cooled to T=0'C (ice bath). HCl (4M in dioxane, 0.3 ml, 0.94 mmol, 1.2 eq.) was added and the reaction mixture was stirred at room temperature overnight. The solid formed was filtered, washed with $Et_2O$ and dried to afford the HCl salt of SUL-128 (300 mg, 90% pure) as a white solid (mixture of diastereomers).

$^1$H-NMR ($CDCl_3$, in ppm): 1.20-1.90 (m, 7H), 2.12 (s, 6H), 2.17 (s, 3H), 2.20-2.90 (m, 9H), 3.4-3.65 (m, 2H). $M^+$=320.1

Synthesis of 2,6-Diisopropylcyclohexa-2,5-diene-1,4-dione

Propofol 100 g, 561 mmol) was dissolved in DMF (250 mL). The solution was cooled to 0° C. while stirring. Salcomine (16.6 g, 51 mmol; 9 mol %) was added and the resulting reaction mixture was stirred 112 h overnight while warming to room temperature. The reaction mixture was poured in water (7 L). The resulting slurry was extracted with heptanes (5×1 L). The combined organic extracts were dried with $Na_2SO_4$. Concentration of the solution under vacuum afforded the crude 2,6-diisopropylcyclohexa-2,5-diene-1,4-dione (62.5 g; 325 mmol; 58% yield) as an oil. The product was used in the next step without further purification.

Synthesis of 2,6-Diisopropylbenzene-1,4-dio

Crude 2,6-diisopropylcyclohexa-2,5-diene-1,4-dione (62.5 g, 325 mmol) was dissolved in dichloromethane (300 mL) and methanol (100 mL). The solution was cooled to 0° C. with an ice bath. Sodium borohydride (4.5 g, 182 mmol) was added in portions. After the addition was complete the reaction mixture was stirred at room temperature overnight. Acetone (150 mL) was added to quench the excess of sodium borohydride. After 30 minutes stirring 2N aq. HCl (200 mL) was added. After stirring for 45 minutes the mixture was extracted with ethyl acetate (4×400 mL). The combined organic layers were dried with $Na_2SO_4$. Concentration of the solution under vacuum afforded crude 2,6-diisopropylbenzene-1,4-diol (64 g, 330 mmol) as a red oil in quantitative yield. The product was used in the next step without further purification.

Synthesis of 3,5-Diisopropyl-2-methylbenzene-1,4-diol

A mixture of 2,6-diisopropylbenzene-1,4-diol (64 g, 0.33 mol), paraformaldehyde (9.8 g, 0.327 mol), $SnCl_2$ (217.9 g, 1.15 mol), concentrated aq. 37% HCl (0.6 L) and diisopropyl ether (2.5 L) was heated to reflux for 4 hours. After cooling to room temperature overnight the biphasic mixture was separated. The aqueous layer was extracted with TBME (2000 mL). The combined organic fractions were washed with 1N aq. HCl (1000 mL), water (1000 mL) and brine (1000 mL). The organic fractions were dried with $Na_2SO_4$ and concentrated under vacuum to give a 50:35 mixture of 3,5-diisopropyl-2-methylbenzene-1,4-diol and 2,6-diisopropyl-3,5-dimethylbenzene-1,4-diol (61 g oil) according to GCMS analysis. Purification by chromatography on silica gel (1200 mL) eluting with ethyl acetate/heptanes=97.5:2.5 (4000 mL), 95:5 (4000 mL) gave 3,5-diisopropyl-2-methylbenzene-1,4-diol 6 (16.6 g, 79.8 mmol; 24%: 83% pure) as an oil.

Synthesis of Methyl 6-hydroxy-5,7-diisopropyl-2,8-dimethylchroman-2-carboxylate 3,5-diisopropyl-2-methylbenzene-1,4-diol (10.6 g, 50.9 mmol; 83% pure) was dissolved in methyl methacrylate (20 mL, 186 mmol). The solution was transferred to a Teflon tube in a Berghof reactor. Aqueous formaldehyde (10 mL; 37% wt. solution, stabilized with 10-15% MeOH) was added and the reaction mixture was heated to 180° C. (internal temperature) in the closed reactor for 5 hours while stirring. After cooling to ca. 40° C. the reaction mixture was poured in MeOH (200 mL) and the mixture was concentrated under vacuum. Purification by chromatography on silica gel (600 mL) eluting with ethyl acetate/heptanes=95:5 (5000 mL; TLC: Rf~0.2; spot stained with iodine vapor) gave the desired pure product methyl 6-hydroxy-5,7-diisopropyl-2,8-dimethylchroman-2-carboxylate (10.0 g, 31.3 mmol, 61%).

Synthesis of 6-Hydroxy-5,7-diisopropyl-2,8-dimethylchroman-2-carboxylic acid (SUL-118)

A mixture of purified methyl 6-hydroxy-5,7-diisopropyl-2,8-dimethylchroman-2-carboxylate (8.3 g, 25.9 mmol) and lithium hydroxide monohydrate (4.3 g, 102.5 mmol; 4 eq.) in MeOH (100 mL), THF (100 mL) and water (25 mL) was heated for 30 minutes at ambient pressure while rotating with a rotary evaporator in a warm water bath at 60° C. The organic solvents were evaporated under vacuum. Water (150 mL) was added to the residue, followed by acetic acid (10 mL). A light orange mixture was obtained. Extraction with ethyl acetate (3×100 mL), drying of the combined organic fractions with $Na_2SO_4$ and concentration under vacuum gave the crude product as an orange solid. The solids were stirred with tBME (150 mL). A beige solid precipitated and an orange solution was obtained. Heptane (250 mL) was added and the mixture was stirred for 15 minutes. The mixture was filtered over a glass filter. The residual solids were washed with heptanes (2×50 mL) on the filter under suction. Drying of the solids under vacuum at 60° C. gave pure 6-hydroxy-5,7-diisopropyl-2,8-dimethylchroman-2-carboxylic acid (SUL-118) as an off-white solid (3.1 g, 10.13 mmol; 39%, 100% pure).

$^1$H-NMR ($CDCl_3$, in ppm): 1.38 (t, 12H), 1.52 (s, 3H), 1.87 (m, 1H), 2.20 (s, 3H), 2.30 (m, 1H), 3.20 (m, 1H), 3.38 (m, 1H). M+=307.10

Synthesis of SUL 119 (2-(hydroxymethyl)-5,7-diisopropyl-2,8-dimethylchroman-6-ol)

A solution of methyl 6-hydroxy-5,7-diisopropyl-2,8-dimethylchroman-2-carboxylate (500 mg, 1.56 mmol) in THF (12 mL) was added over 5 minutes with a syringe via a rubber septum to $LiAlH_4$ (238 mg, 6.26 mmol; 4 eq.), pre-weighed in a dry 3-mecked 100 mL round bottomed flask under inert nitrogen atmosphere while stirring at room temperature. The exothermic addition of the ester was accompanied with gas evolution. After the addition was complete the resulting grey suspension was heated to reflux. After 3 hours the heating was stopped and the reaction was quenched by dropwise addition of EtOAc (6 mL; exothermic). Water (5 mL) was added in small portions, followed by 2N HCl (2 mL) followed by EtOAc (25 mL). The mixture was poured on $Na_2SO_4$ (ca. 50 g) and the slightly yellow organic layer was separated from the two-phase mixture. The aqueous phase was washed with EtOAc (50 mL) and the combined organic fractions were concentrated under vacuum to give the crude alcohol (530 mg) as a clear oil. Heptane (100 mL) was added and after concentration under vacuum the 2-(hydroxymethyl)-5,7-diisopropyl-2,8-dimethylchroman-6-ol (248 mg, 0.85 mmol, 54%, LCMS: 95.5% pure).

M+=293.2

Synthesis of SUL 139 (2-(4-(6-hydroxy-5,7-diisopropyl-2,8-dimethylchroman-2-carbonyl)piperazin-1-yl)acetic acid SUL-137 (440 mg, 1.17 mmol, 1 eq.,) was dissolved in MeOH (50 ml) and glyoxalic acid (216 mg, 2.35 mmol, 2 eq.) was added. The resulting mixture was stirred for 1 hour at room temperature and, subsequently, $NaBH_3CN$ (183 mg, 2.94 mmol, 2.5 eq.) was added. The reaction mixture was stirred at room temperature overnight. Acetic acid (few ml) was added and after stirring at room temperature for 0.5-1 hour, the reaction mixture was concentrated. The residue obtained was dissolved in EtOAc, washed with $H_2O$ (2×), dried, filtered and concentrated to afford SUL-139 (500 mg, 1.16 mmol, 98%, 91-92% pure) as a light yellow solid.

$^1$H-NMR ($CD_3OD$, in ppm): 1.33 (dd, 12H), 1.59 (s, 3H), 1.62 (m, 1H), 2.09 (s, 3H), 2-5-3.0 (m, 7H), 3.1-3.6 (m, 4H), 3.81 (bs, 2H), 4.28 (bs, 2H). M$^+$=433.2.

Synthesis of SUL 136 (2-(4-(6-hydroxy-2,5,7,8-tetramethylchroman-2-carbonyl) piperazin-1-yl) acetic acid)

A 250 ml three-necked flask equipped with two septa (left and right) and a stopcock was charged with SUL-136 (15.5 g, 38.4 mmol) and THF/water (240 ml THF+80 ml water). The clear solution was stirred and degassed for at least 30 minutes by argon-bubbling, using an inlet tube equipped with a long syringe needle through the left septum; the right septum was equipped with a short needle and functioned as outlet. The degassed solution (which was maintained under argon) was cooled to 0° C. in an ice-bath and solid anhydrous LiOH (2.3 g, 96 mmol, 2.5 eq.) was added in one portion. The resulting reaction mixture was stirred for 2 hours at 0° C. after which it was neutralized by addition of a MeOH/water (3/1, v/v) slurry of Dowex-50WX8-200 ion-exchange resin; the final pH was approx. 6. The Dowex resin was filtered off with suction and rinsed with 3 portions of MeOH/water (3/1, v/v). The filtrate was reduced in vacuo and to the wet product was added approx. 100 ml water. The resulting white aqueous suspension was freeze-dried overnight to afford SUL-136 (13.48 g, 93%. LCMS: 99.6%) as a white solid.

1H-NMR (CD3OD, in ppm)): 1.60 (s, 3H), 1.65 (m, 1H), 2.05 (s, 3H), 2.10 (s, 6H), 2.55 (m, 2H), 2.62 (m, 1H), 3.0, (bs, 4H), 3.40 (bs, 2H), 3.65 (bs, 2H), 4.25 (bs, 2H). M+=377.1

Synthesis of SUL 144 ((2S)-1-(6-hydroxy-2,5,7,8-tetramethylchroman-2-carbonyl)pyrrolidine-2-carboxylic acid)

(2S)-methyl 1-(6-hydroxy-2,5,7,8-tetramethylchroman-2-carbonyl)pyrrolidine-2-carboxylate (diastereomer 1, 3.5 g, 9.7 mmol) was dissolved in THF/$H_2O$ (60/20 mL). $N_2$ was bubbled through the solution for 1 h. The mixture was cooled in an ice-bath and LiOH.$H_2O$ (1.01 g, 24.2 mmol, 2.5 eq.) was added. The reaction mixture was stirred under $N_2$ at RT overnight. Dowex-50WX8-200 (washed 4× with MeOH/$H_2O$ 3:1) was added as a slurry in MeOH/$H_2O$ (3:1) until the pH=6. The mixture was filtered, washed with MeOH/$H_2O$ (3:1) and concentrated in vacuo. Demi $H_2O$ (50 mL) was added to the concentrate and the solution was freeze dried affording SUL-144 (3.4 g, 9.7 mmol, quant, 99.7% pure) as a off-white foam.

1H-NMR (CDCl3): 1.60 (s, 3H), 1.65-2.30 (m, 14H), 2.60 (m, 2H), 2.81 (m, 1H), 3.49 (m, 1H), 4.01 (t, 1H), 4.50 (d, 1H). M+=348.1

Example 2

Introduction (6-hydroxy-2,5,7,8-tetramethylchroman-2-yl)(piperazin-1-yl)methanone or SUL121 has been shown to be very effective in reducing ischemia and reperfusion damage in the rat kidney. In this model, the blood flow to the kidney was stopped for an extended period where after blood flow was restored. This model is known to strongly induce renal ROS production. SUL121 is believed to be a $H_2S$ inducer, a compound with diverse actions including inhibition of the respiratory chain thereby reducing ROS formation. One of the underlying mechanisms may be the induction of the $H_2S$ producing enzyme CBS and increased expression of GDF 15.

Given its effectiveness in the model of renal ischemia and reperfusion, it was hypothesized that compound SUL 121 will also protect the kidney in an experimental model of obesity induced Type 2 diabetes (T2DM). Therefore, the effects of SUL121 on the development of albuminuria and renal damage in the mouse Type 2 diabetes model was studied. For the study, the db/db mouse model was employed. The db/db mouse does not have a functional leptin receptor and therefore develop obesity induced diabetes. Diabetes starts at the age of 6-8 weeks and adequate levels of kidney damage and albuminuria can be observed at the age of 18 weeks.

To study the effects of SUL121 on the development of diabetes, treatment with SUL121 started from the age of 10 weeks until the age of 18 weeks. In addition, to study the effects of SUL 121 on healthy animals, control mice were treated similarly. A non-treated control group was included in the study, to serve as healthy untreated control. Drug and vehicle were administered by implantation of osmotic minipumps at the age of 10 and 14 weeks.

Materials and Methods

Chemicals and Formulation

Cell culture grade DMSO was obtained from Sigma-Aldrich (Zwijndrecht, the Netherlands). 0.9% sterile saline solutions were from Baxter (Utrecht, the Netherlands). (6-hydroxy-2,5,7,8-tetramethylchroman-2-yl)(piperazin-1-yl)methanone (SUL121) was supplied by Sulfateq BV, Groningen, the Netherlands supplied in a formulation of 500 mM in 100% DMSO corresponding to 177 g/l. Osmotic minipumps (Alzet, USA) are resistant to DMSO concentrations≤50%. Therefore, the solubility of SUL121 was tested in 50% DMSO in saline solution. SUL121 was completely soluble in 50% DMSO up to a concentration of 12.6 g/l. Alzet model 2004 pumps were loaded with 200 μl of 12.6 g/1 SUL121 solution or with 200 ul 50% DMSO solution (vehicle). According to pump specifications 6 µl of SUL121 was administered per day, resulting in a daily dose of 2.2 mg/kg/day for a 35 gram mouse.

Test Animals

Male db/db mice (n=16) and lean heterozygous control animals (n=16) were purchased from Harlan UK (strain JAX000642). All mice were housed individually. Water and food were given ad-libitum. Four groups of mice were investigated:
1) db/db+vehicle (diabetic control)
2) db/db+Sul121 (treated diabetic group)
3) wt+vehicle (non-diabetic control)
4) wt+Sul121 (to study effect of drug only)

Drug and vehicle were administered by implantation of osmotic minipumps at the age of 10 (t=0) and 14 weeks (t=4). Metabolic cages and blood pressure measurements were performed every two weeks. Blood samples could not be obtained by cheek puncture, therefore blood was collected from the retro orbital plexus at the age of 10 (t=0) and 12 weeks (t=2). At the age of 18 weeks (t=8) all animals were terminated and blood was collected by cardiac puncture.

Urinary Measurements

Urinary glucose concentrations were measured by the glucose oxidase method with a specific electrode from 24-h urine collections after the samples were stored in −20° C. The urinary creatinine concentration was measured by standard laboratory methods (Jaffe method without deproteinization, DiaSys Diagnostic Systems, Holzheim, Germany). The median values of the 24-h urine collections and of the albumin-to-creatinine ratio were calculated. In addition, mouse albumin levels in urine were determined manually using a mouse albumin Elisa kit (Abcam, Cambridge, UK). Urinary hydrogen peroxide levels were determined using an Amplex Red H2O2 assay kit (Life technologies, Leusden, the Netherlands).

Blood Pressure Measurement

Arterial blood pressure was measured in anaesthetized mice (2% isoflurane) by means of the tail-cuff method (PS-200A; Riken-Kaihatsu; Tokyo, Japan). For each animal, blood pressure values represent the mean of three to ten recordings obtained in a single session.

Histology

Kidneys fixed in paraformaldehyde were used for α-smooth muscle actin (α-SMA) staining. Four-micrometer sections were cut, deparaffinized, hydrated, and processed with 1 mmol/EDTA (pH 9.0) for antigen retrieval. All steps were according to the Vector MOM kit protocol. To evaluate prefibrosis after diabetic injury, sections were stained for α-SMA (mouse monoclonal anti-α-smooth muscle actin; Sigma Chemical, St. Louis, Mo.) in 1:100 dilution, with MOM diluent certifying negative staining.

Peroxidase activity was developed by incubation with AEC (Dako) The expression of -SMA was measured using computer-assisted morphometry. Total staining was evaluated at a magnification of ×200. Glomeruli and arteries were excluded from measurements. α-SMA staining was divided by the area measured and expressed as a percentage. At least 10 cortical fields were measured to obtain an average score per animal.

To evaluate the renal damage after diabetic injury, sections were stained for KIM-1, a marker of tubular damage (rabbit polyclonal, Dr. H. van Goor, University Medical Center Groningen). Paraffin sections were dewaxed and subjected to antigen retrieval in 0.1 M Tris.HCl buffer, pH 9, by overnight incubation at 80° C. A two-step immunoperoxidase technique was used. Control slides, in which the primary antibody was replaced with PBS, were consistently negative. Evaluation of the staining's and morphometric analysis were performed in a blinded manner.

Organ Bath Experiments with the Isolated Aorta

Freshly isolated thoracic aortic rings (1.5-2 mm in length) were mounted on 200-µm stainless wires in individual myograph baths (Danish Myo Technology, Aarhus, Denmark). Briefly, baths containing 6 ml Krebs solution were warmed to 37° C. and preequilibrated and continuously aerated with 95% $O_2$-5% $CO_2$ to maintain pH at 7.4. The length of the aortic strips was assessed by microscopy. Aortic rings were equilibrated for 40 min until they were at a steady baseline. Rings were then primed and checked for viability by two consecutive stimulations with KCl (60 mM) followed by washings and renewed stabilization to obtain reproducible contractile responses.

Vascular Protocol

Contraction responses were measured as cumulative concentration-response curves to phenylephrine (PE; 10 nM-100 µM) followed by a single concentration of KCl (90 mM). Endothelium-dependent relaxation was assessed by obtaining concentration-response curves to ACh (10 nM-300 µM) in rings precontracted with PE (1 µM) followed by stimulation with a high concentration of the NO donor sodium nitroprusside (SNP; 0.1 mM) to assess maximal endothelium-independent dilation.

To study the role of the endothelium in vasoconstrictor effects, rings were denuded by removing the endothelial cell layer by rubbing the luminal side of the vessel with a moistened wire. To examine the contribution of different EDRFs in modulating vasoconstrictor responses and mediating endothelium-dependent relaxation, inhibitors of PG and NO synthesis were used. To this end, PG components were assessed by preincubating rings (20 min.) with the nonspecific cyclooxygenase inhibitor indomethacin (10 µM). The NO component was examined by subsequent incubation with both NO synthesis inhibitor NG-monomethyl-L-arginine (L-NMMA; 1 µM) and indomethacin. The remaining ACh-mediated relaxation was attributed to an unidentified EDHF.

Morphological Analysis

Four-micrometer-thick formalin fixed sections were deparaffinized and stained for periodic acid-Schiff (PAS) for quantification of focal glomerulosclerosis (FGS) and tubular injury. FGS was semiquantitatively scored in a blinded fashion by determining the level of mesangial expansion and focal adhesion in each quadrant in a glomerulus and expressed on a scale from 0 to 4. If 25% of the glomerulus was affected, it was scored as 1, 50% as 2, 75% as 3, and 100% as 4. In total, 50 glomeruli per kidney were analyzed, and the total FGS score was calculated by multiplying the score by the percentage of glomeruli with the same FGS score. Thus the total FGS score ranged from 0 to 200.

Histological changes of tubular morphology were evaluated by assessment of four markers of damage: tubular necrosis, loss of brush border, denudation of basement membrane, and intraluminal casts. Each parameter was graded on a scale from 0 to 3, according to the extent of the injury (0: <5%; 1: 5-25%; 2: 25-75%; and 3: >75%). In total, 30 tubules per kidney were analyzed, and the histological score was calculated. Thus total histological score ranged from 0 to 90.

Data Processing

Contractions to KCl and PE are given in milliNewtons. Relaxation responses to ACh and SNP are expressed as percentages of the preconstriction with PE. In addition to that, the area under each individual curve (AUC; in arbitrary units) was determined for ACh-induced relaxation (SigmaPlot version 10.0, Systat Software, San Jose, Calif.). The AUC was used to present total endothelium-dependent relaxation and for the subsequent analysis of differences in ACh-mediated relaxation with and without inhibitors present to estimate the contribution of the different EDRFs, i.e., PGs for the part sensitive to cycloxygenase inhibition with indomethacin, NO for the part sensitive to NOS inhibition with L-NMMA, and EDHF by means of exclusion of PG and NO (34).

Statistical Evaluation

Data are presented as means±SE, and n refers to the number of animals in each group. Statistical analysis was done with SPSS 16.0.2 for Windows (SPSS, Chicago, Ill.). Differences between full concentration-response curves were tested with repetitive ANOVA; differences between points were tested with one-way ANOVA. P values of <0.05 (two tailed) were considered as statistically significant.

Results

Metabolic Data

Metabolic data are shown in FIG. 1. As expected the diabetic mice had a significantly higher body weight compared to their lean controls (FIG. 1, panel A). Diabetic mice gradually lost weight from week 4 and later. SUL121 treatment did not affect body weight at any time point.

Water intake and urine output (FIG. 1, panel B and C) were closely linked and significantly higher in the diabetic mice. At week 8, SUL 121 treated diabetic mice had significantly lower urine production and water intake then the diabetic controls (urine 23.1±2.5 and 11.2±3.8 g, water intake 22.5±2.5 and 10.9±3.9 g for diabetic control and diabetic SUL121, respectively). At all other time points, SUL121 did not significantly affect urine output and water intake.

Non-fasting blood glucose levels were significantly higher in the diabetic db/db mice compared to the wild type control mice (FIG. 1, panel D). During the course of the experiment, non-fasting blood glucose levels in the diabetic animals rose from 27.5±2.5 and 27.2±1.3 (diabetic control and diabetic SUL121 treated, respectively) to 35.8±2.4 and 35.3±1.1 mM, indicating a severe and progressive diabetic state. Treatment with SUL121 did not affect blood glucose levels.

At weeks 0, 2 and 6, blood pressure was measured (FIG. 1, panel E). At week 0, mean blood pressure in the diabetic animals was higher than in non-diabetic wild type mice. SUL 121 treatment lowered blood pressure at week 2 in non-diabetic wild type mice at week 2. SUL 121 treatment did not affect blood pressure at week 6. In diabetic mice, SUL121 treatment did not affect blood pressure.

Effects of SUL121 Treatment on Organ Weight

Figure 2:
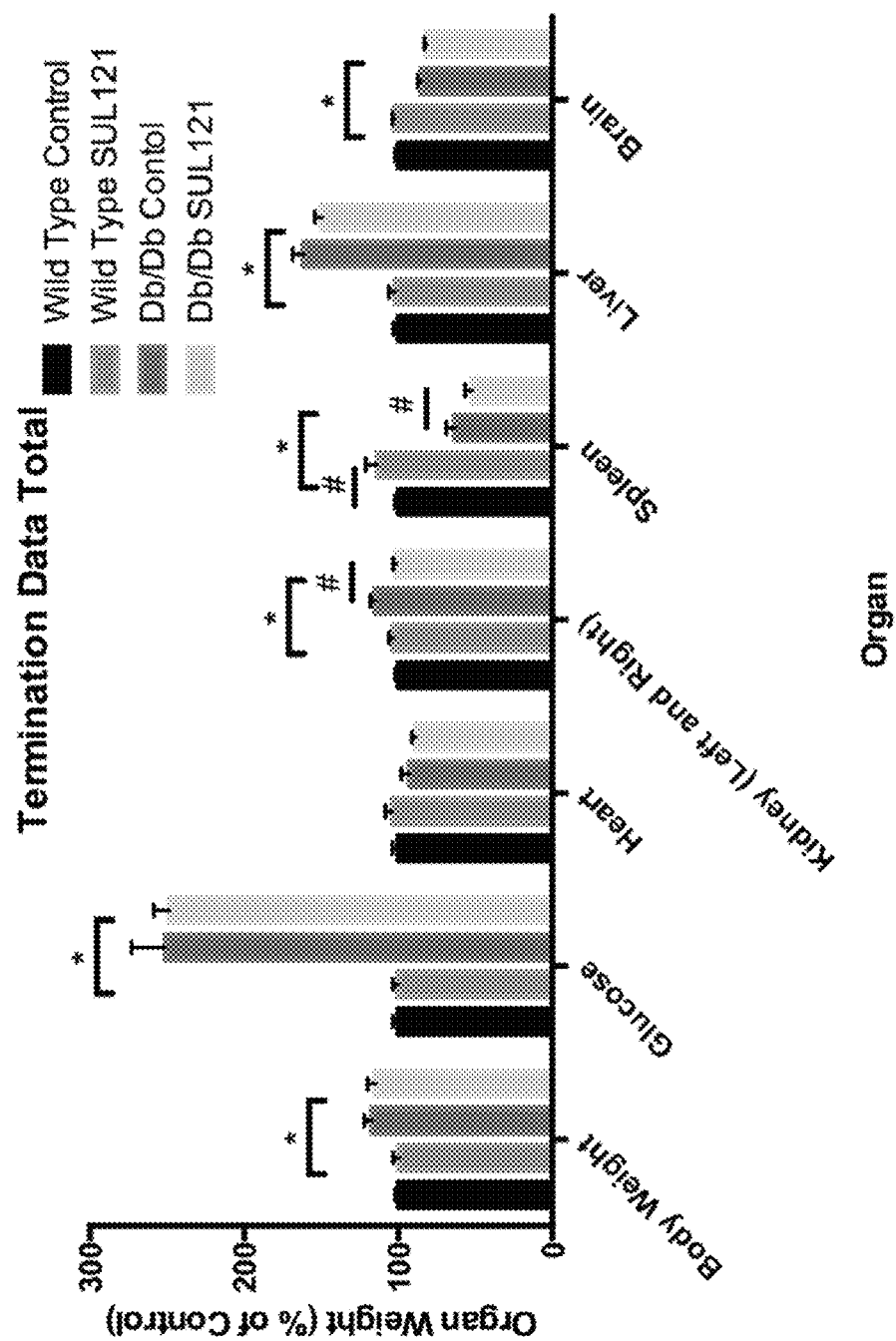
FIG. 2 shows organ weights at termination. *$p<0.05$ diabetic SUL121 vs diabetic control. # $p<0.05$ diabetic vs wild type control.

After 8 weeks of treatment, mice were terminated and organ weights were measured (FIG. 2). In the diabetic control mice, both left and right kidney weights were significantly increased, indicating kidney hypertrophy. SUL 121 treatment normalized kidney weights to non-diabetic control values.

Effects of SUL121 on Renal Function

Figure 3:
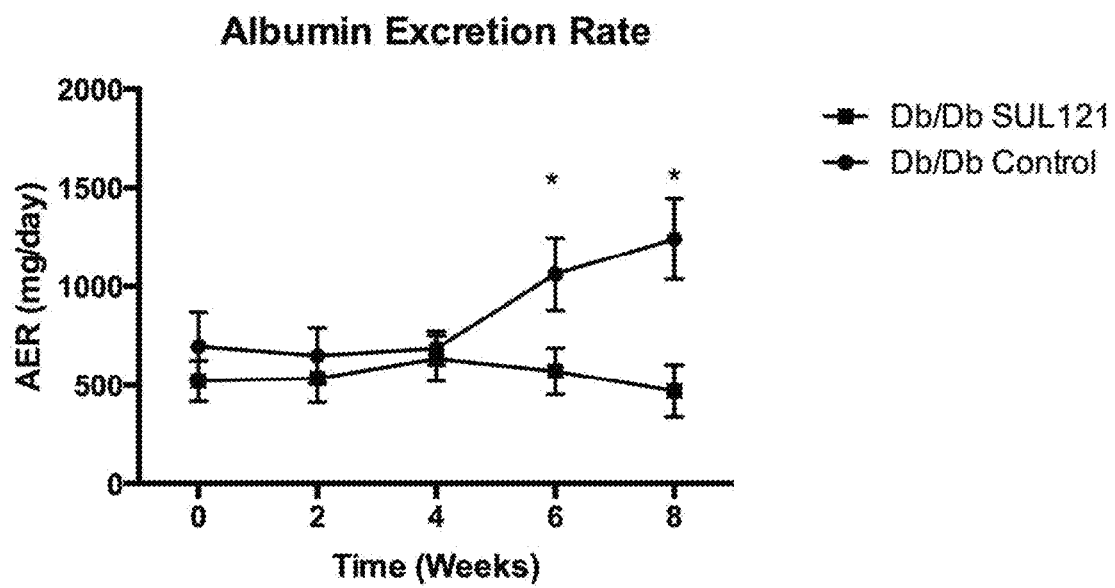
FIG. 3 shows urinary albumin excretion and ACR ratios for diabetic animals. *,# $p<0.05$ diabetic SUL121 vs diabetic control.
Figure 3:
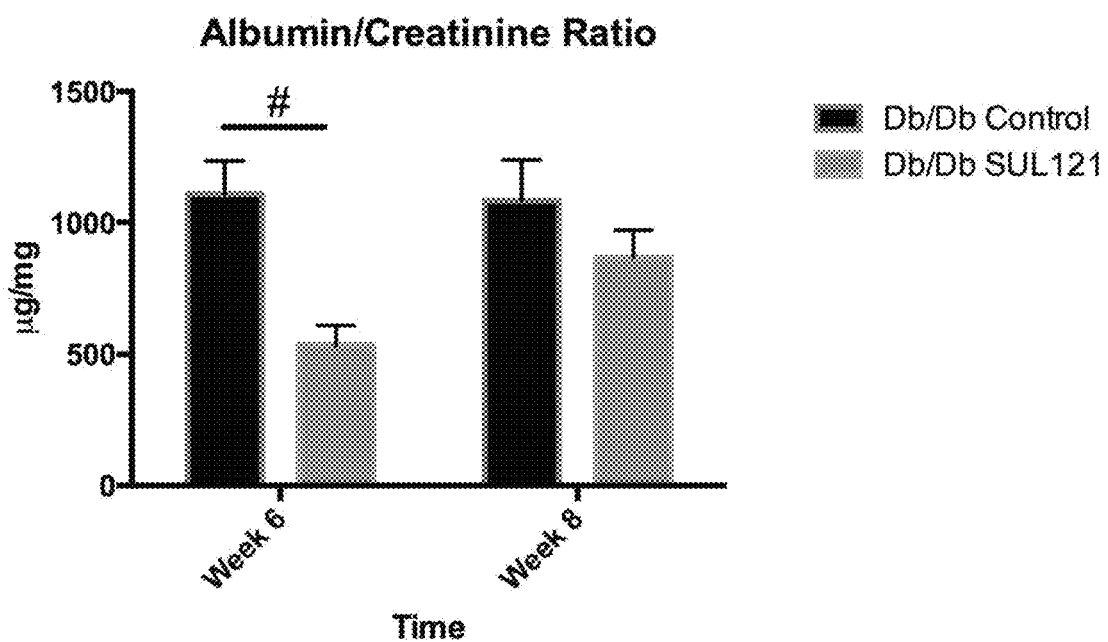

To test whether SUL 121 treatment could reduce renal damage, albumin leakage into the urine was measured at all time points for diabetic animals. Total albumin excretion per day (AER) was calculated by multiplying urinary albumin concentration with daily urinary output (FIG. 3A). Treatment with SUL 121 prevented the progression in AER in diabetic animals at weeks 6 and 8. AER in non-diabetic controls was only measured at week 8 and was significantly lower than for diabetic animals (non-diabetic control: 33.8±5.1 mg/day, non-diabetic SUL121 treated: 31.3±4.6 mg/day). SUL121 treatment did not affect AER in non-diabetic animals.

In addition, the albumin/creatinine ratio (ACR) was determined at weeks 6 and 8 (FIG. 3B). At week 6, ACR in SUL121 treated diabetic mice was significantly lower than in diabetic control mice (1107±130 and 534±79 µg/mg for diabetic control and diabetic SUL121 treated, respectively). At week 8, ACR in SUL 121 treated animals was also lower than in diabetic control mice, but this did not reach statistical significance. (1084±156 and 866±91 µg/mg for diabetic control and diabetic SUL 121 treated, respectively).

ACR in wild type animals at week 8 was significantly lower than for diabetic animals and was unaffected by SUL121 treatment (71±9 and 55±6 µg/mg for wild type control and wild type SUL 121 treated, respectively).

Effects of SUL121 on Renal Histology

Figure 4:
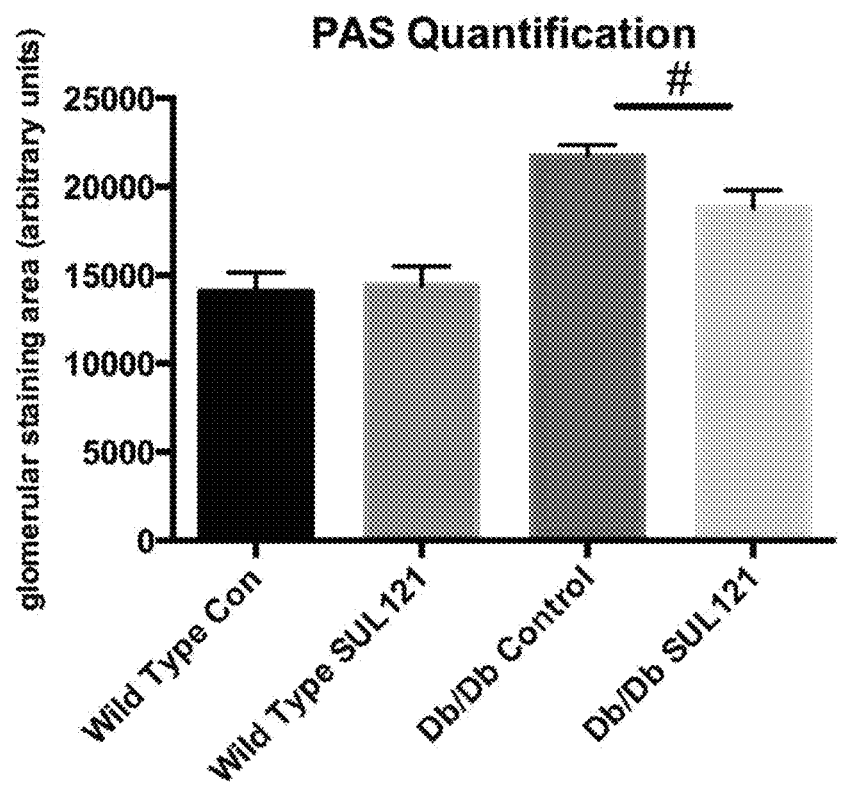
FIG. 4 shows FGS scores in diabetic animals are significantly reduced by SUL121 treatment.

As SUL121 had a profound effect on albuminuria, a PAS staining was performed to investigate the effects of SUL 121 on focal glomerular sclerosis (FGS) in all animals (FIG. 4). As expected FGS scores were increased in diabetic db/db mice. Treatment with SUL 121 significantly lowered FGS scores in diabetic mice.

Vascular Function in Diabetes

Impaired release of relaxing factors from the endothelium (endothelial dysfunction) is an established phenomenon in the db/db model of diabetes. To establish the effects of SUL 121 treatment on endothelial function, mouse aortic rings were precontracted with phenylephrine (PE) and subsequently relaxed with increasing concentrations of acetylcholine (ACh). Dose effect curves were constructed (FIG. 5A), demonstrating an impaired relaxation to ACh in db/db mice compared to controls (max. relaxation of PE 39.2±6.5 and 9.2±1.6% for db/db and control, respectively). In the SUL121 treated diabetic group, relaxations were restored to control levels (11.3±2.3%). In non-diabetic controls, SUL121 treatment did not affect vascular relaxations (9.2±1.6%). Taken together, these data demonstrate that SUL 121 treatment was able to prevent the development of endothelial dysfunction in the db/db model of diabetes.

Figure 5:
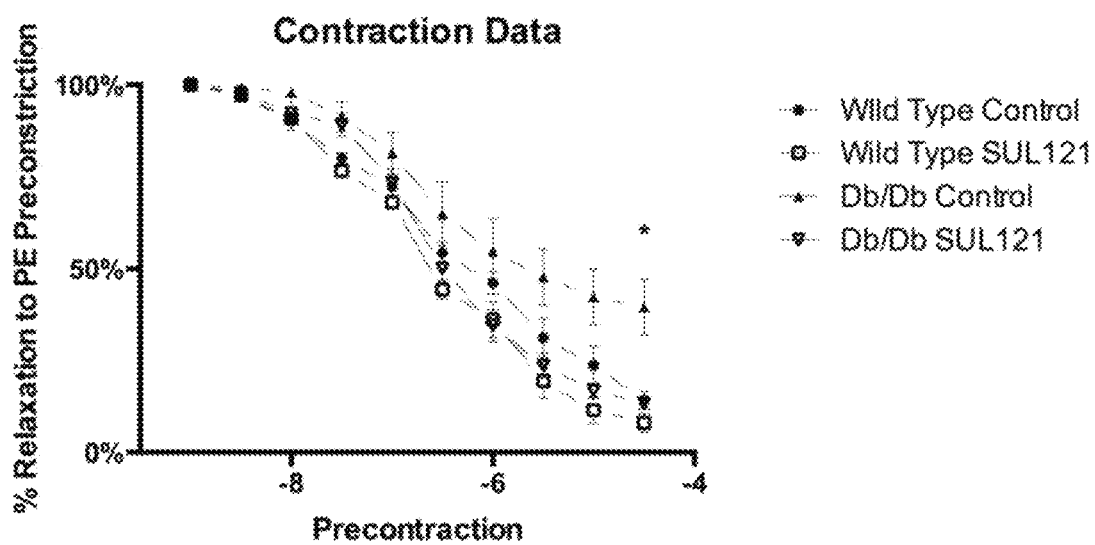
FIG. 5 shows that SUL121 treatment restores endothelium mediated relaxation.
Figure 5:
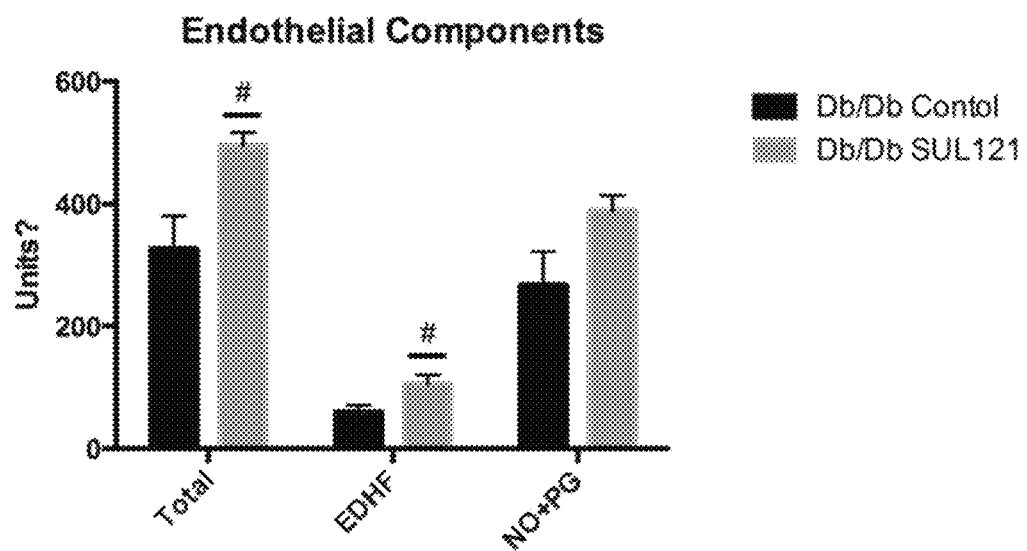

To further investigate the endothelial components involved in vascular relaxation, dose response curves were constructed using specific inhibitors for eNOS (L-NMMA) and cyclooxygenase (indomethacin) and the relative contribution of each component was calculated (FIG. 5B). In the diabetic animals, SUL121 improved total relaxation by significantly increasing EDHF. In addition, SUL 121 caused a non-significant (p=0.06) increase in the NO and prostaglandin components.

Effects of SUL121 on ROS Production in Diabetes

Figure 6:
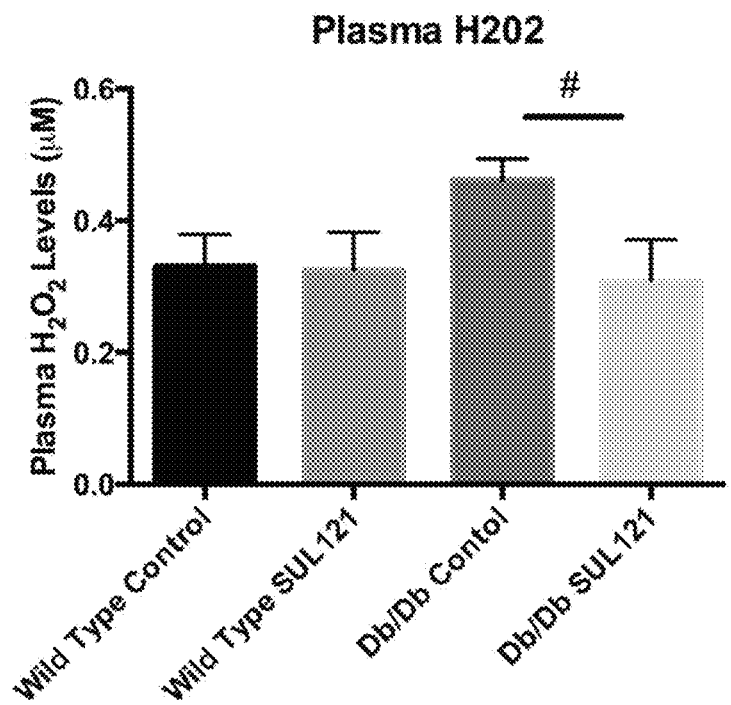
FIG. 6 shows that SUL121 treatment normalized plasma $H_2O_2$ levels in diabetes.

Enhanced reactive oxygen species (ROS) production is a well-established phenomenon in diabetes. To study the effects of SUL121 treatment on ROS production, hydrogen peroxide, a stable metabolite of ROS, was measured in plasma (FIG. 6). SUL 121 treatment normalized $H_2O_2$ levels in plasma.

In-Vitro Assessment of SUL121 Mediated Protection in Diabetes

To further explore the mechanisms through which SUL 121 mediates renal protection in diabetes, an in-vitro model of diabetes was employed. For this, mouse renal mesangial cells were exposed to conditions simulating type 2 diabetes (high glucose and insulin). Exposure to high glucose/insulin increased intracellular ROS levels by approximately 70%

Figure 7:
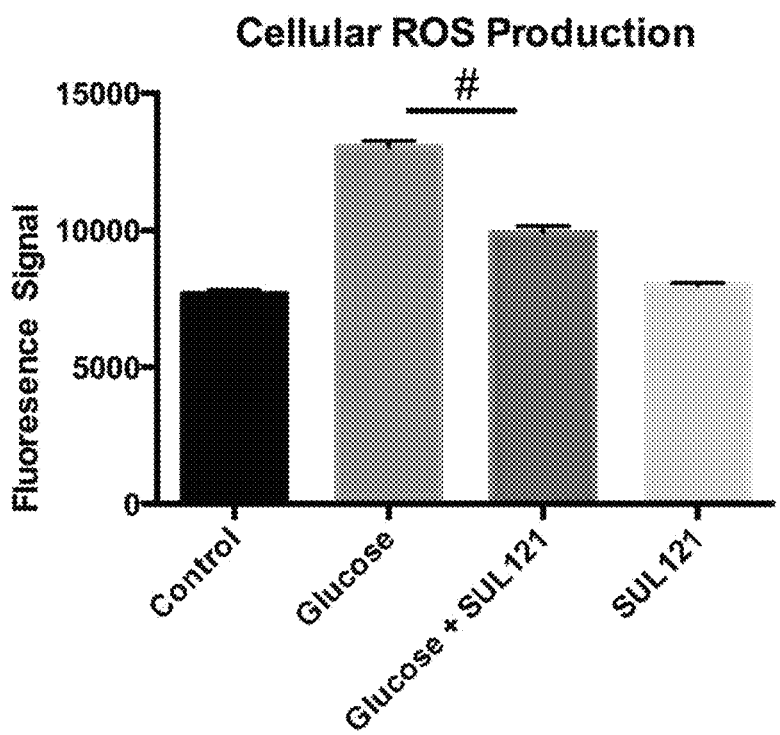
FIG. 7 shows that SUL121 treatment normalized high glucose induced cellular ROS production.

(FIG. 7). Interestingly, this increase could be substantially inhibited if cells were pretreated with SUL121 (p<0.05). SUL 121 alone did not affect intracellular ROS production.

Correlations

Figure 8:
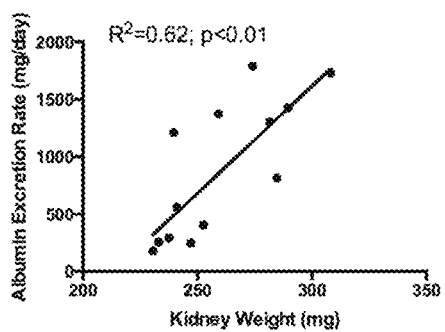
FIG. 8 shows correlations between different parameters.
Figure 8:
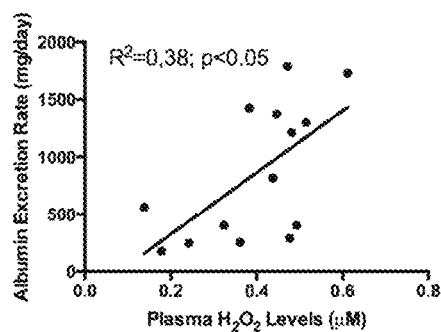
Figure 8:
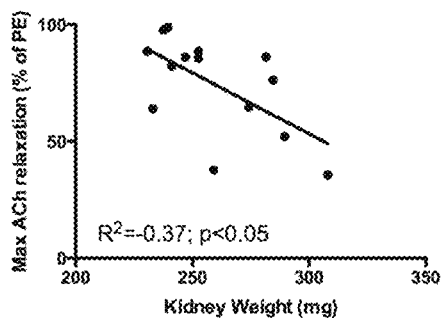
Figure 8:
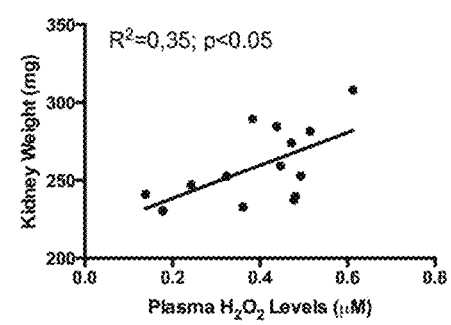
Figure 8:
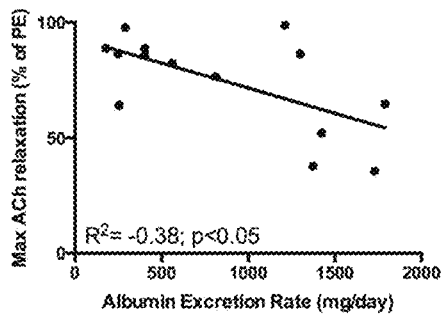

To determine whether kidney hypertrophy was related to functional changes in the kidney, a correlation analysis was performed between kidney weight and albumin excretion in all diabetic animals combined (FIG. 8, panel A). A significant positive correlation was found between both markers (p<0.05). As SUL121 normalized endothelial function in diabetic animals, the maximum relaxation levels were correlated to acetylcholine to kidney weight (FIG. 8, panel B) and to albumin excretion (FIG. 8, panel C). Both correlation were significant (p<0.05).

As SUL121 inhibited $H_2O_2$ levels in plasma, also $H_2O_2$ was correlated to albumin excretion (FIG. 8, panel D) and to kidney weight (FIG. 8, panel E). Both correlations were significant (p<0.05). $H_2O_2$ levels in plasma did not correlate with maximum relaxation levels to acetylcholine (data not shown).

The invention claimed is:

1. A method of treating or prophylaxis of diabetic kidney damage in a subject, comprising administering to the subject a therapeutically effective amount of a compound according to the formula (II)

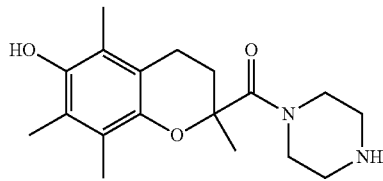 [SMILES: Cc1c(C)c2c(c(C)c1O)CCC(C)(C(=O)N1CCNCC1)O2]

(6-hydroxy-2,5,7,8-tetramethylchroman-2-yl)(piperazin-1-yl)methanone or a pharmaceutically acceptable salt or base thereof, wherein endothelial function is restored, thereby treating or prophylaxis of the diabetic kidney damage.

2. The method of treating or prophylaxis of diabetic kidney damage according to claim 1, wherein said diabetic kidney damage is diabetic nephropathy.

* * * * *